(12) United States Patent
Rao et al.

(10) Patent No.: US 7,504,358 B2
(45) Date of Patent: Mar. 17, 2009

(54) NICKEL-SUBSTITUTED AND MIXED NICKEL- AND COBALT-SUBSTITUTED CHROMIUM OXIDE COMPOSITIONS, THEIR PREPARATION, AND THEIR USE AS CATALYSTS AND CATALYSTS PRECURSORS

(75) Inventors: Velliyur Nott Mallikarjuna Rao, Wilmington, DE (US); H. David Rosenfeld, Drumore, PA (US); Allen C. Sievert, Elkton, MD (US); Shekhar Subramoney, Hockessin, DE (US); Munirpallam Appadorai Subramanian, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 770 days.

(21) Appl. No.: 10/523,226

(22) PCT Filed: Aug. 21, 2003

(86) PCT No.: PCT/US03/26327

§ 371 (c)(1), (2), (4) Date: Jan. 31, 2005

(87) PCT Pub. No.: WO2004/018095

PCT Pub. Date: Mar. 4, 2004

(65) Prior Publication Data

US 2005/0227865 A1    Oct. 13, 2005

Related U.S. Application Data

(60) Provisional application No. 60/405,221, filed on Aug. 22, 2002.

(51) Int. Cl.
*B01J 23/00* (2006.01)
*C07C 19/08* (2006.01)
*C07C 21/00* (2006.01)

(52) U.S. Cl. .................. 502/315; 502/319; 570/164; 570/166; 570/169; 570/172; 570/176

(58) Field of Classification Search .............. 502/315, 502/319; 570/169, 164, 166, 172, 176
See application file for complete search history.

(56) References Cited

U.S. PATENT DOCUMENTS

| | | | |
|---|---|---|---|
| 3,258,500 A | 6/1966 | Swamer et al. |
| 3,804,778 A | 4/1974 | Salindres et al. |
| 3,992,325 A | 11/1976 | Knaak |
| 4,843,181 A | 6/1989 | Gumprecht et al. |
| 5,036,036 A | 7/1991 | Lerou |
| 5,185,482 A | 2/1993 | Manzer |
| 5,345,017 A | 9/1994 | Rao et al. |
| 5,523,500 A | 6/1996 | Cheminal et al. |
| 5,559,069 A | 9/1996 | Rao et al. |
| 5,763,698 A | 6/1998 | Manzer et al. |

| | | | |
|---|---|---|---|
| 2001/0011061 A1 | 8/2001 | Scott et al. |
| 2002/0006374 A1 | 1/2002 | Kourtakis et al. |

(Continued)

FOREIGN PATENT DOCUMENTS

AU    A-29972/92    6/1993

(Continued)

OTHER PUBLICATIONS

U.S. Appl. No. 10/523,228, Rao et al.

(Continued)

*Primary Examiner*—Porfirio Nazario Gonzalez

(57) ABSTRACT

A crystalline alpha-chromium oxide where from about 0.05 atom % to about 2 atom % of the chromium atoms in the alpha-chromium oxide lattice are substituted by nickel atoms, and optionally, additional chromium atoms in the alpha-chromium oxide lattice are substituted by trivalent cobalt atoms (provided that the total amount of the nickel atoms and the trivalent cobalt atoms in the alpha-chromium oxide lattice is no more than 6 atom %) is disclosed. Also disclosed is a chromium-containing catalyst composition comprising as a chromium-containing component the crystalline substituted alpha-chromium oxide; and a method for preparing a composition comprising the crystalline substituted alpha-chromium oxide. The method comprises (a) co-precipitating a solid by adding ammonium hydroxide to an aqueous solution of a soluble divalent nickel salt, a soluble trivalent chromium salt, and optionally, a soluble divalent or trivalent cobalt salt, that contains at least three moles of nitrate per mole of chromium in the solution, has a nickel concentration of from about 0.05 mole % to about 2 mole % of the total of nickel, chromium, and cobalt in the solution, and has a combined concentration of nickel and cobalt of no more than 6 mole % of the total of nickel, chromium, and cobalt in the solution; and after at least three moles of ammonium per mole of chromium has been added to the solution; (b) collecting the co-precipitated solid formed in (a); (c) drying the collected solid; and (d) calcining the dried solid. Also disclosed is a chromium-containing catalyst composition comprising a chromium-containing component prepared by treating said crystalline substituted alpha-chromium oxide with a fluorinating agent; and a process for changing the fluorine distribution (i.e., content and/or arrangement) in a hydrocarbon or halogenated hydrocarbon in the presence of a catalyst. The process involves using as the catalyst a composition comprising the crystalline substituted alpha-chromium oxide and/or the treated substituted alpha-chromium oxide.

14 Claims, 8 Drawing Sheets

U.S. PATENT DOCUMENTS

2002/0155947 A1 10/2002 Lacroix et al.

FOREIGN PATENT DOCUMENTS

| AU | A-80340/94 | 6/1995 |
|----|------------|--------|
| EP | 0 546 883 B1 | 6/1993 |
| EP | 0 641 598 A2 | 3/1995 |
| EP | 0 847 801 A1 | 6/1998 |
| JP | 04-262372 | 9/1992 |
| WO | WO 2004/018093 A2 | 3/2004 |
| WO | WO 2004/018396 A1 | 3/2004 |
| WO | WO 2004/018397 | 3/2004 |

OTHER PUBLICATIONS

U.S. Appl. No. 10/523,223, filed Aug. 22, 2002, Rao et al.

U.S. Appl. No. 10/523,227.

S. Music et. al., Formation and Characterization of the Solid Solutions, J. Materials Science, 1996, pp. 4067-4076, vol. 31.

Bhattacharya et. al., An X-Ray Diffraction and Mossbauer Study of Nano-Crystalline FE2O3-CR2O3 Soild Solutions, J. Materials Science, 1997, pp. 560-577, vol. 32.

Chamberland et. al., Preparation and Properties of Nicro, J. of Applied Physics, 1969, pp. 434-435, vol. 40.

Muller et. al., X-Ray Diffraction Study of the Chromates of Nickel, Magnesium and Cadmium, Zeitschrift Fur Kristallgraphie, 1969, pp. 112-120, BD. 130, S.

Prince E., Structure of Nickel Chromite, J. of Applied Physics, 1961, pp. 68S-69S, vol. 32.

Nowotny et. al., Boundary Layer Chemical Diffusion and Lattice Parameter of Undoped and CR-Doped NIO., Bulletin of the Polish Academy of Sciences, Chemistry, 1985, pp. 111-119, vol. 33.

Bracconi et. al., Etude Des Proprietes Structurales Des Oxydes Spinelles Des Systems CO-O et CO-CR-OANN. Chim. FR., 1979, pp. 331-338, vol. 4.

Hanck et. al., Structural and Thermal Stability Studues of LIZN2CRO4 and CO2CRO4, J. Inorg. Nucl. Chem., 1971, pp. 63-73, vol. 33.

Castiglioni et. al., Synthesis and Properties of Spinel-Type CO-CU-MG-ZN-CR Mixed Oxides, J. Solid State Chemistry, 2000, pp. 526-532, vol. 152.

Nowotny et al., Segregation and Near-Surface Diffusion for Undoped and CR-Doped CoO, J. Am. Ceram. Soc, 1982, pp. 192-196, vol. 65.

Zhang et al., Cobalt Doped Chromium Oxides as Cathode Materials for Secondary Lithium Batteries, Journal of Power Sources, 1999, pp. 121-127, vol. 83.

Shannon et. al., Effective Ionic Radii in Oxides and Fluorides, Acta Crystallographica, 1969, pp. 925-945, vol. B25.

Chemical Abstracts., 118: 9 397, vol. 118, p. 138 (1993).

NICKEL-SUBSTITUTED AND MIXED NICKEL- AND COBALT-SUBSTITUTED CHROMIUM OXIDE COMPOSITIONS, THEIR PREPARATION, AND THEIR USE AS CATALYSTS AND CATALYSTS PRECURSORS

This application represents a national filing under 35 U.S.C. 371 of International Application No. PCT/US03/26327 filed Aug. 21, 2003, claiming priority of U.S. Provisional Application No. 60/405,221 filed Aug. 22, 2002.

FIELD OF THE INVENTION

This invention relates to chromium-containing compositions and their preparation and use for the catalytic processing of hydrocarbons and/or halogenated hydrocarbons.

BACKGROUND

It is well known that $\alpha\text{-}Cr_2O_3$ and $\alpha\text{-}Fe_2O_3$ have in common the structure of $\alpha\text{-}Al_2O_3$ (corundum) with the $M^{+3}$ ions occupying octahedral sites in the hexagonally close-packed oxide lattice. In contrast, NiO and CoO have distorted cubic lattices while $Co_3O_4$ has a normal spinel structure. These basic structures are described in standard treatises; see, for example, pages 538, 543-545, and 550 of *Structural Inorganic Chemistry* by A. F. Wells, 5th ed. Clarendon Press, Oxford, UK (1986). γ-Chromium oxide ($CrO_{2.44}$) is described in Wilhelmi, *Acta Chemica Scandinavica*, Vol. 22, pages 2565-2573 (1968).

Numerous mixed metal oxides have been prepared in which the cation sites of the lattice are occupied by different metal ions. For example, solid solutions of the type $(Cr_m Fe_{1-m})_2O_3$ are known where $0<m<1$. These materials have been prepared by standard ceramic or sol-gel techniques as described by Music, et al. in *J. Materials Science*, Vol. 31, pages 4067-4076 (1996) and by Bhattacharya, et al. in *J. Materials Science*, Vol. 32, pages 577-560 (1997).

Mixed Cr—Ni oxides are known (see e.g., Chamberland and Cloud, *J. of Applied Physics*, Vol. 40, pages 434-435 (1969) where $NiCrO_3$ which has a corundum-type structure is discussed; Muller, et. al., *Z. Kristallogr., Kristallgeom., Kristallphys., Kristallchem.*, Vol. 130, pages 112-120 (1969); Prince, *J. of Applied Physics*, Vol. 32, pages 68S-69S (1961); and Nowotny et al., *Bulletin of the Polish Academy of Sciences*, Chemistry, Vol. 33, pages 111-119 (1985). Mixed Cr—Co oxides having a spinel structure are known (see e.g., Bracconi et al. in *Ann. Chim. Fr.*, Vol. 4, pages 331-338 (1979) and Hanck and Laitinen in *J. Inorg. Nucl. Chem.*, Volume 33, pages 63-73 (1971)).

$CrCoO_3$ is referenced as an interconnector material in a fuel cell assembly (see Chem. Abs. 118:9397). Various mixed metal oxides containing cobalt and chromium are also disclosed in Castiglioni, et al., *J. Solid State Chemistry*, Vol. 152, 526-532 (2000); Nowotny et al., *J. Am. Ceram. Soc.*, Vol. 65, pages 192-196 (1982); and Zhang et al., *Journal of Power Sources*, Vol. 83, pages 121-127 (1999).

Certain metal oxides are used as catalysts and/or catalyst precursors in the manufacture of fluorinated hydrocarbons. Chromium(III) oxide in particular is useful as it has been found that it may be fluorinated by HF at elevated temperature to a give mixture of chromium fluoride and chromium oxyfluoride species which are active catalysts for conversion of C—Cl bonds to C—F bonds in the presence of HF. This conversion of C—Cl bonds to C—F bonds by the action of HF, known generally as halogen exchange, is a key step in many fluorocarbon manufacturing processes.

Chromium oxide compositions useful as catalyst precursors may be prepared in various ways or may take various forms. Chromium oxide suitable for vapor phase fluorination reactions may be prepared by reduction of Cr(VI) trioxide, by dehydration of Guignet's green, or by precipitation of Cr(III) salts with bases (see U.S. Pat. No. 3,258,500). Another useful form of chromium oxide is hexagonal chromium oxide hydroxide with low alkali metal ion content as disclosed in U.S. Pat. No. 3,978,145. Compounds such as $MF_4$ (M=Ti, Th, Ce), $MF_3$ (M=Al, Fe, Y), and $MF_2$ (M=Ca, Mg, Sr, Ba, Zn) have been added to hexagonal chromium oxide hydroxide to increase catalyst life as disclosed in U.S. Pat. No. 3,992,325. A form of chromium oxide that is a precursor to a particularly active fluorination catalyst is that prepared by pyrolysis of ammonium dichromate as disclosed in U.S. Pat. No. 5,036,036.

The addition of other compounds (e.g., other metal salts) to supported and/or unsupported chromium-based fluorination catalysts has been disclosed. Australian Patent Document No. AU-A-80340/94 discloses bulk or supported catalysts based on chromium oxide (or oxides of chromium) and at least one other catalytically active metal (e.g., Mg, V, Mn, Fe, Co, Ni, or Zn), in which the major part of the oxide(s) is in the crystalline state (and when the catalyst is a bulk catalyst, its specific surface, after activation with HF, is at least 8 $m^2/g$). The crystalline phases disclosed include $Cr_2O_3$, $CrO_2$, $NiCrO_3$, $NiCrO_4$, $NiCr_2O_4$, $MgCrO_4$, $ZnCr_2O_4$ and mixtures of these oxides. Australian Patent Document AU-A-29972/92 discloses a mass catalyst based on chromium and nickel oxides in which the Ni/Cr atomic ratio is between 0.05 and 5. U.S. patent application Publication No. US2001/0011061 A1 discloses chromia-based fluorination catalysts (optionally containing Mg, Zn, Co, and Ni) in which the chromia is at least partially crystalline. Fluorinated catalysts containing cobalt and chromium in combination (e.g. impregnated on a support) are among those disclosed in U.S. Pat. No. 5,185,482. U.S. Pat. No. 5,559,069 discloses homogeneously dispersed multiphase catalyst compositions characterized by dispersed phases of certain divalent metal fluorides (certain fluorides of Mn, Co, Zn, Mg, and/or Cd) and certain trivalent metal fluorides (fluorides of Al, Ga, V, and/or Cr).

There remains a need for halogen exchange catalysts that can be used for processes such as the selective fluorination and chlorofluorination of saturated and unsaturated hydrocarbons, hydrochlorocarbons, hydrochlorofluorocarbons, and chlorofluorocarbons, the fluorination of unsaturated fluorocarbons, the isomerization and disproportionation of fluorinated organic compounds, the dehydrofluorination of hydrofluorocarbons, and the chlorodefluorination of fluorinated hydrocarbons.

SUMMARY OF THE INVENTION

This invention provides a crystalline alpha-chromium oxide where from about 0.05 atom % to about 2 atom % of the chromium atoms in the alpha-chromium oxide lattice are substituted by nickel atoms, and optionally, additional chromium atoms in the alpha-chromium oxide lattice are substituted by trivalent cobalt atoms, provided that the total amount of the nickel atoms and the trivalent cobalt atoms in the alpha-chromium oxide lattice is no more than 6 atom %.

This invention also provides a chromium-containing catalyst composition comprising as a chromium-containing component said crystalline substituted alpha-chromium oxide.

This invention also provides a method for preparing a composition comprising said crystalline substituted alpha-chromium oxide. The method comprises (a) co-precipitating a solid by adding ammonium hydroxide (aqueous ammonia) to an aqueous solution of a soluble divalent nickel salt, a soluble trivalent chromium salt, and optionally, a soluble divalent or trivalent cobalt salt, that contains at least three moles of nitrate (i.e., $NO_3^-$) per mole of chromium (i.e., $Cr^{+3}$) in the solution, has a nickel concentration of from about 0.05 mole % to about 2 mole % of the total of nickel, chromium, and cobalt (if present) in the solution, and has a combined concentration of nickel and cobalt (if present) of no more than 6 mole % of the total of nickel, chromium, and cobalt (if present) in the solution; and after at least three moles of ammonium (i.e., $NH_4^+$) per mole of chromium (i.e., $Cr^{+3}$) has been added to the solution; (b) collecting the co-precipitated solid formed in (a); (c) drying the collected solid; and (d) calcining the dried solid.

This invention also provides a chromium-containing catalyst composition comprising a chromium-containing component prepared by treating said crystalline substituted alpha-chromium oxide with a fluorinating agent (e.g., hydrogen fluoride).

This invention also provides a process for changing the fluorine distribution (i.e., content and/or arrangement) in a hydrocarbon or halogenated hydrocarbon in the presence of a catalyst. The process is characterized by using as the catalyst a composition comprising at least one chromium-containing component selected from the group consisting of said crystalline substituted alpha-chromium oxides and said treated substituted alpha-chromium oxides.

DETAILED DESCRIPTION

Figure 1:
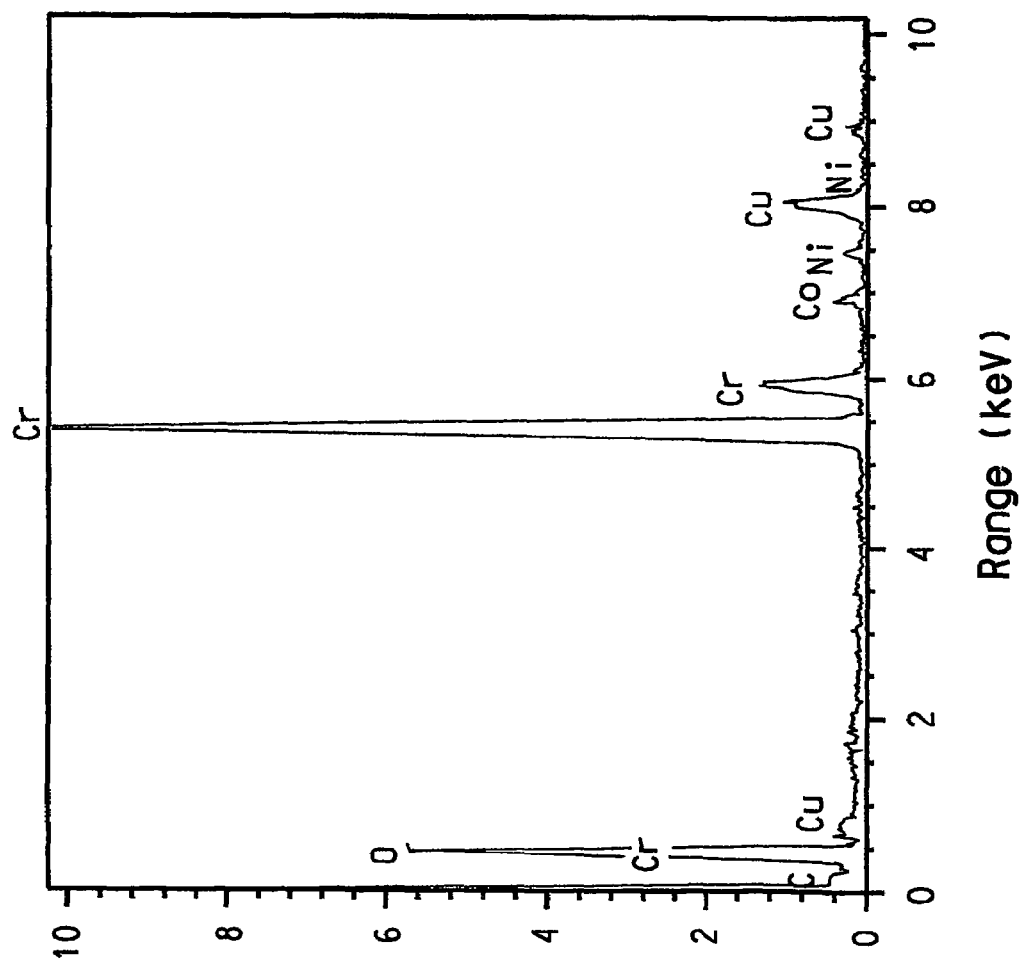
FIG. 1 represents an energy dispersive spectroscopy spectrum for a sample of mixed nickel- and cobalt-substituted alpha-chromium oxide nominally containing 3 atom % cobalt and 2 atom % nickel.

New compositions of this invention comprise substituted alpha-chromium oxide containing nickel, or both nickel and cobalt, which retains the corundum structure. This invention includes a catalytic composition comprising said crystalline substituted $\alpha$-$Cr_2O_3$. The nickel content of the substituted alpha-chromium oxide is from about 0.05 atom % to about 2 atom % of the total of the nickel, chromium, and cobalt (if present) in the alpha-chromium oxide. The total of the nickel and cobalt in the alpha-chromium oxide is no more than 6 atom % of the total of the nickel, chromium, and cobalt. The crystalline substituted alpha-chromium oxides have the general formula $\alpha$-$Ni_xCo_yCr_{2-x-y}O_3$ where x is 0.001 to 0.04 and y is 0 to 0.12-x.

The compositions of the present invention may be prepared by the method described above using co-precipitation. In the typical co-precipitation technique, an aqueous solution of nickel(II) and chromium(III) salts, and optionally cobalt(II) or cobalt(III) salts, is prepared. The relative concentrations of nickel(II), cobalt, and chromium(III) salts in the aqueous solution is dictated by the bulk mole percent nickel and cobalt relative to chromium desired in the final catalyst. The concentration of chromium(III) in the aqueous solution is typically in the range of from 0.3 to 3 molar (moles per liter) with 0.75-1.5 molar being a preferred concentration. Chromium (III) salts suitable for preparation of the aqueous solution are the nitrate, sulfate, acetate, formate, oxalate, phosphate, bromide, and chloride and various hydrated forms of these salts. Other chromium(III) salts that are useful for the preparation of the aqueous solutions include hexacoordinate complexes of the formula $[CrL_{6-z}Az]^{+3-z}$ where each L is a neutral (i.e., uncharged) ligand selected from the group consisting of $H_2O$, $NH_3$, C1-C4 primary, secondary, or tertiary organic amines, a C1-C4 alkyl nitrites, or pyridine, where each A is an anionic ligand selected from the group consisting of fluoride, chloride, bromide, iodide, hydroxide, nitrite, and nitrate, and where z has a value of from 0 to 3 inclusive. Included are neutral bidentate ligands such as ethylene diamine which are equivalent to two L in that they may occupy two coordination sites. Also included are anionic bidentate ligands such as $C_1$-$C_4$ carboxylate which may occupy two coordination sites. Also included are dianionic ligands such as sulfate which are equivalent to two A ligands and may occupy more than one coordination site.

Salts containing alkali metals such as chromium potassium sulfate are not preferred because the presence of alkali metals can hinder catalyst activity (see U.S. Pat. No. 4,843,181). Chromium(VI) precursors, such as $CrO_3$, though not preferred, may be used but require reduction to Cr(III) with a compound such as ethanol before precipitation.

Chromium(III) nitrate, or its hydrated forms such as [Cr$(NO_3)_3(H_2O)_9$], are the most preferred chromium(III) salt for preparation of said aqueous solution.

Nickel(II) salts suitable for preparation of the aqueous solution are the nitrate, acetate, acetylacetonate, sulfate, formate, oxalate, bromide, chloride, and fluoride and various hydrated forms of these salts. Nickel(II) nitrate hydrate (e.g., [Ni$(NO_3)_2(H_2O)_6$]) is the most preferred nickel(II) salt.

Cobalt(II) salts suitable for preparation of the aqueous solution are the nitrate, sulfate, formate, oxalate, bromide, and chloride and various hydrated forms of these salts. Salts containing alkali metals such as cobalt potassium bis(sulfate) are not preferred because the presence of alkali metals can hinder catalyst activity. Cobalt(II) nitrate hydrate (e.g., [Co$(NO_3)_2(H_2O)_6$]) is the most preferred cobalt(II) salt.

Cobalt(III) salts that are useful for the preparation of the aqueous solutions include hexacoordinate complexes of the formula $[CoL_{6-z} A_z]^{+3-z}$ where each L is a neutral (i.e., uncharged) ligand selected from the group consisting of $H_2O$, $NH_3$, $C_1$-$C_4$ primary, secondary, or tertiary organic amine, a $C_1$-$C_4$ alkyl nitrile, or pyridine, where each A is an anionic ligand selected from the group consisting of fluoride, chloride, bromide, iodide, hydroxide, nitrite, and nitrate, and where a has a value of from 0 to 3 inclusive. Included are neutral bidentate ligands such as ethylene diamine which are equivalent to two L in that they may occupy two coordination sites. Also included are anionic bidentate ligands such as $C_1$-$C_4$ carboxylate which may occupy two coordination sites. Also included are dianionic ligands such as sulfate which are equivalent to two A ligands and may occupy more than one coordination site. Preferred cobalt(III) starting materials are hexammine salts (e.g., $[Co(NH_3)_6]^{+3}$ where the counter ion is chloride or nitrate. Hexaamminecobalt(III) chloride (e.g., $[Co(NH_3)_6]Cl_3]$) is the most preferred cobalt(III) salt.

The aqueous solution of the nickel(II) and chromium(III) salts, and optionally cobalt(II) or cobalt(III) salts, may then be evaporated either under vacuum or at elevated temperature to give a solid which is then calcined.

Preferably, however, the aqueous solution of nickel(II) and chromium(III) salts, and optionally cobalt salts, is then treated with a base such as ammonium hydroxide (aqueous ammonia) to precipitate the nickel and chromium, and optionally cobalt, as the hydroxides. Bases containing alkali metals such as sodium or potassium hydroxide or the carbonates may be used but are not preferred. The addition of ammonium hydroxide to the aqueous solution of nickel(II) and chromium(III) salts, and optionally cobalt salt(s), is typically carried out gradually over a period of 1 to 12 hours. The pH of the solution is monitored during the addition of base. The final pH is typically in the range of 6.0 to 11.0, preferably from about 7.5 to about 9.0, and most preferably from about 8.0 to 8.7. The precipitation of the nickel hydroxide/cobalt hydroxide/chromium hydroxide mixture is typically carried out at a temperature of about 15° C. to about 60° C., preferably from about 20° C. to about 40° C. After the ammonium hydroxide is added, the mixture is typically stirred for up to 24 hours.

Of note are preparations where excess ammonium nitrate (i.e., more than three moles of ammonium nitrate per mole of chromium) is present in the aqueous solution. For example, in addition to the ammonium nitrate already present from reaction of ammonium hydroxide with chromium nitrate, from about 0.1 mole to about 7.0 moles of additional ammonium nitrate per mole of chromium may be added to the solution before, during, or after the co-precipitation of the compositions. Surprisingly, we have found that addition of ammonium nitrate to the precipitated mixture of nickel and chromium, and optionally cobalt, hydroxides prior to the dehydration step decreases the particle size of the $\alpha$-$Ni_x$-$Co_yCr_{2-x-y}O_3$ phase which in turn increases the surface area of that phase and the activity of the catalyst.

After the ammonium nitrate is added to the mixture, it is stirred for about 0.5 to ten hours, preferably one to five hours at a temperature of from about 20° C. to about 60° C. The mixture is then dried and calcined as indicated below.

Other agents that serve this purpose include aqueous hydrogen peroxide (1% to 30% solutions), ozone, peroxy acids such as peroxyacetic acid, and ammonium persulfate. Agents such as halogens may be used but are not preferred. Agents containing alkali metals such as potassium persulfate or sodium perborate may also be used but are not preferred.

After the precipitation of the mixture of nickel, chromium, and optionally cobalt, hydroxides is complete, and the ammonium nitrate or other agents added if desired, the mixture is dried by evaporation.

Optionally, the precipitated mixture of metal hydroxides may be collected and, if desired, washed with deionized water before drying. This may influence the activity of the catalyst.

After the mixture of metal hydroxides has been dried, the nitrate salts are then decomposed by heating the solid from about 250° C. to about 350° C. The resulting solid is then calcined at temperature of from about 375° C. to about 1000° C., preferably from about 400° C. to about 600° C. The calcination temperature can influence the activity of the catalysts and, in turn, the product distribution when the catalysts are used to change the fluorine distribution in hydrocarbons and halogenated hydrocarbons (see Examples 9, 10, 11, and 12).

The calcination is preferably carried out in the presence of oxygen, most preferably in the presence of air.

The metal oxide compositions of this invention may be characterized by well-established analytical techniques including X-Ray absorption spectroscopy (XAS), X-ray powder diffraction (XRD), transmission electron microscopy (TEM), and energy dispersive spectroscopy (EDS). EDS is an analytical tool available in conjunction with scanning or analytical TEM.

After calcination, the resulting nickel-substituted, and optionally cobalt-substituted, crystallites are not visually distinguishable from $\alpha$-$Cr_2O_3$ by TEM. Furthermore, X-ray and electron diffraction studies are entirely consistent with the $\alpha$-$Cr2O3$ structure with some lattice contraction or expansion proportional to the amount of Ni and, if present, Co(III), substituted for Cr(III) in the structure. The compositions are therefore concluded to have the general formula $\alpha$-$Ni_x$-$Co_yCr_{2-x-y}O_3$ where x is from 0.001 to 0.04 and y is from 0 to 0.12-x.

Figure 2:
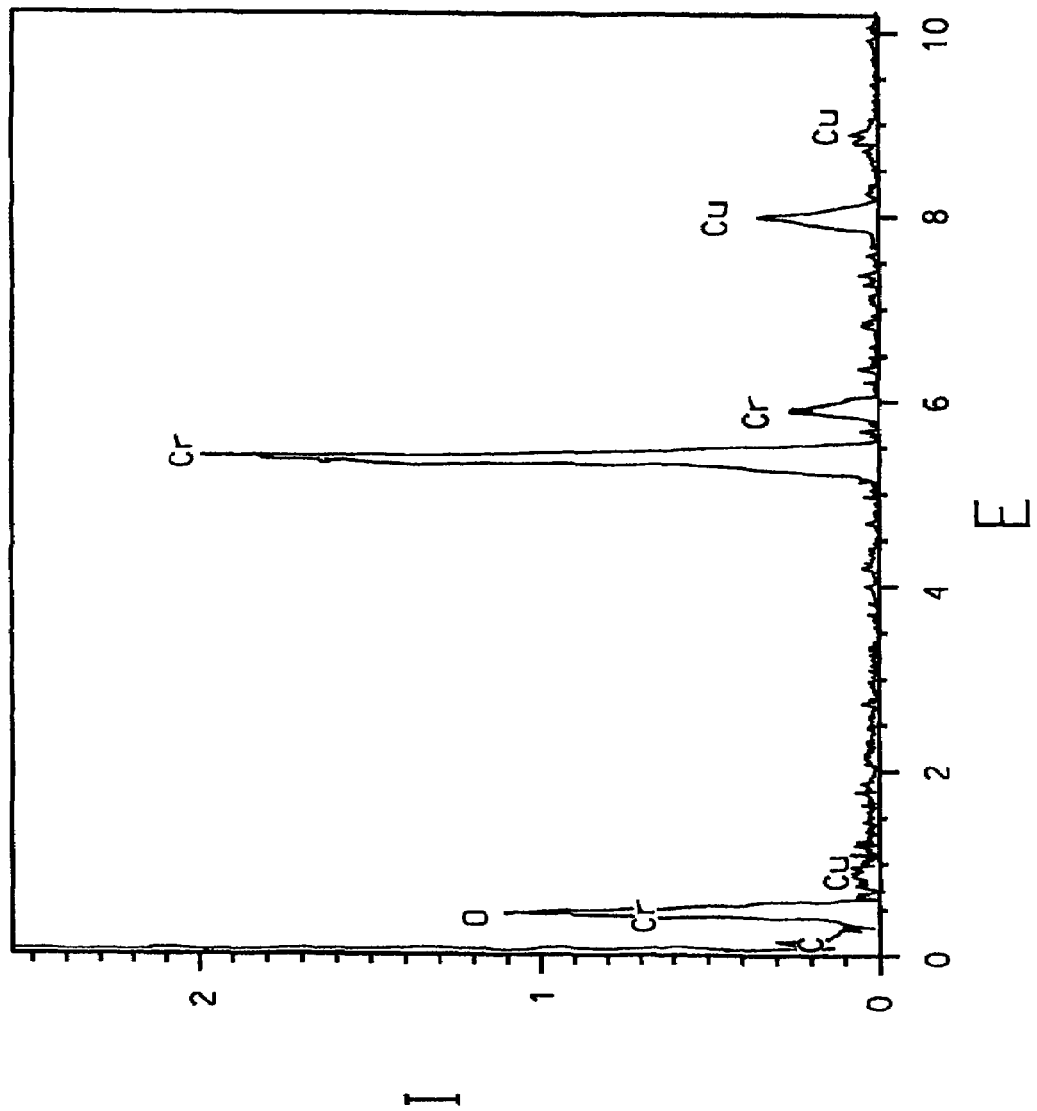
FIG. 2 represents an energy dispersive spectroscopy spectrum for a sample of alpha-chromium oxide without nickel or cobalt substitution.
Figure 3:
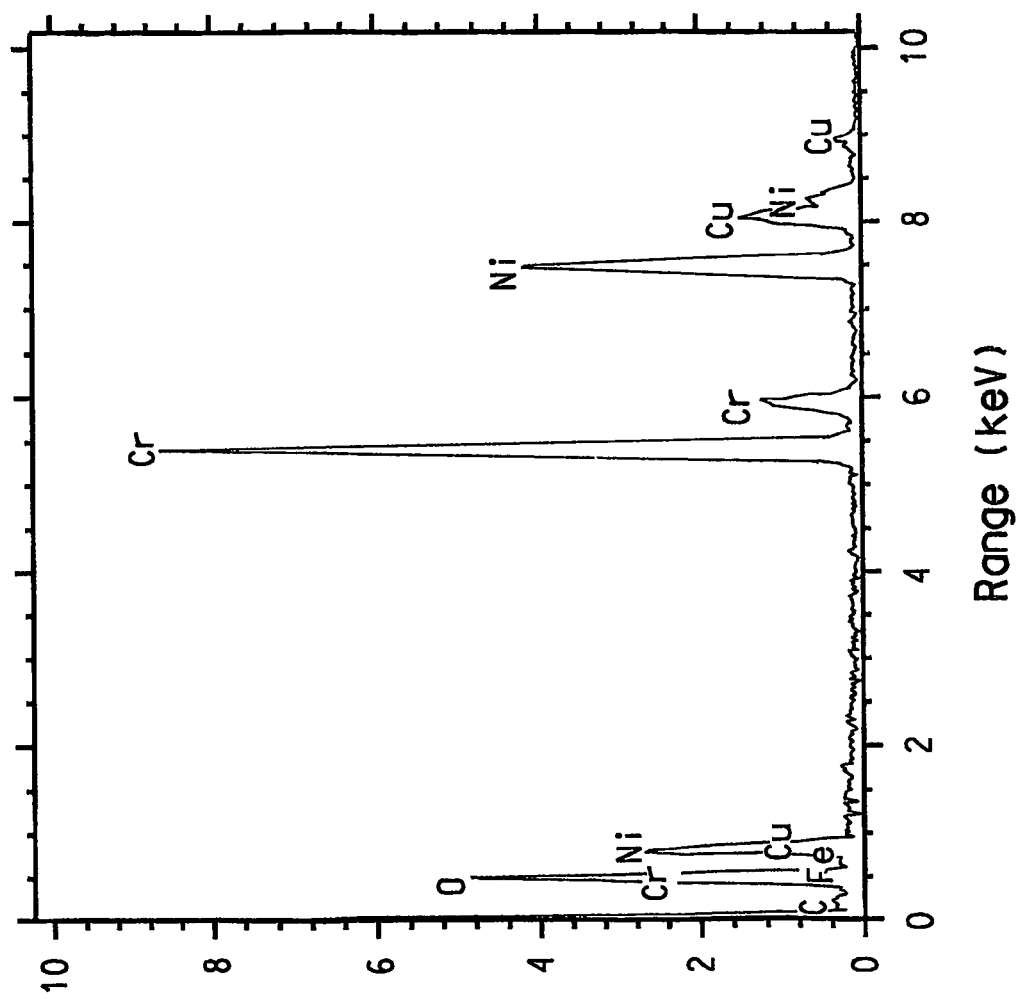
FIG. 3 represents an energy dispersive spectroscopy spectrum for a sample of nickel chromium spinel.
Figure 4:
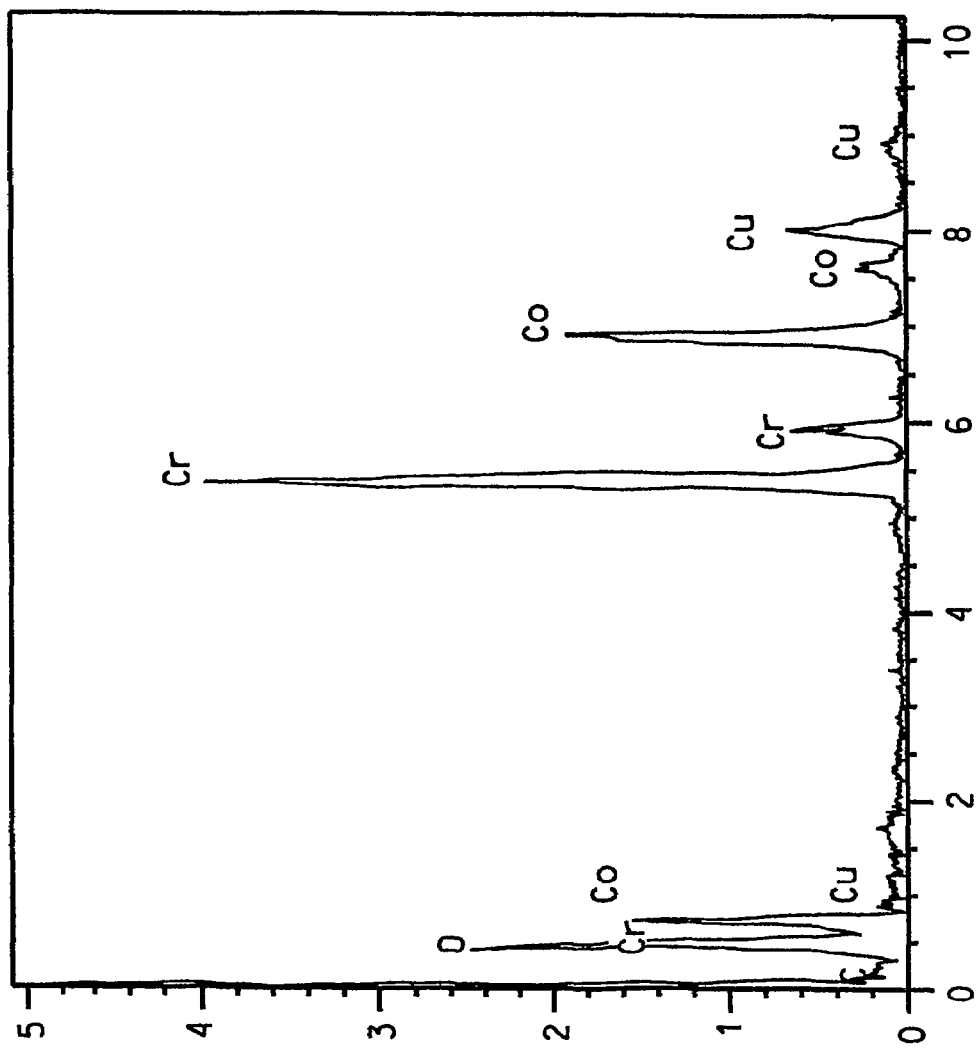
FIG. 4 represents an energy dispersive spectroscopy spectrum for a sample of cobalt chromium spinel.
Figure 5:
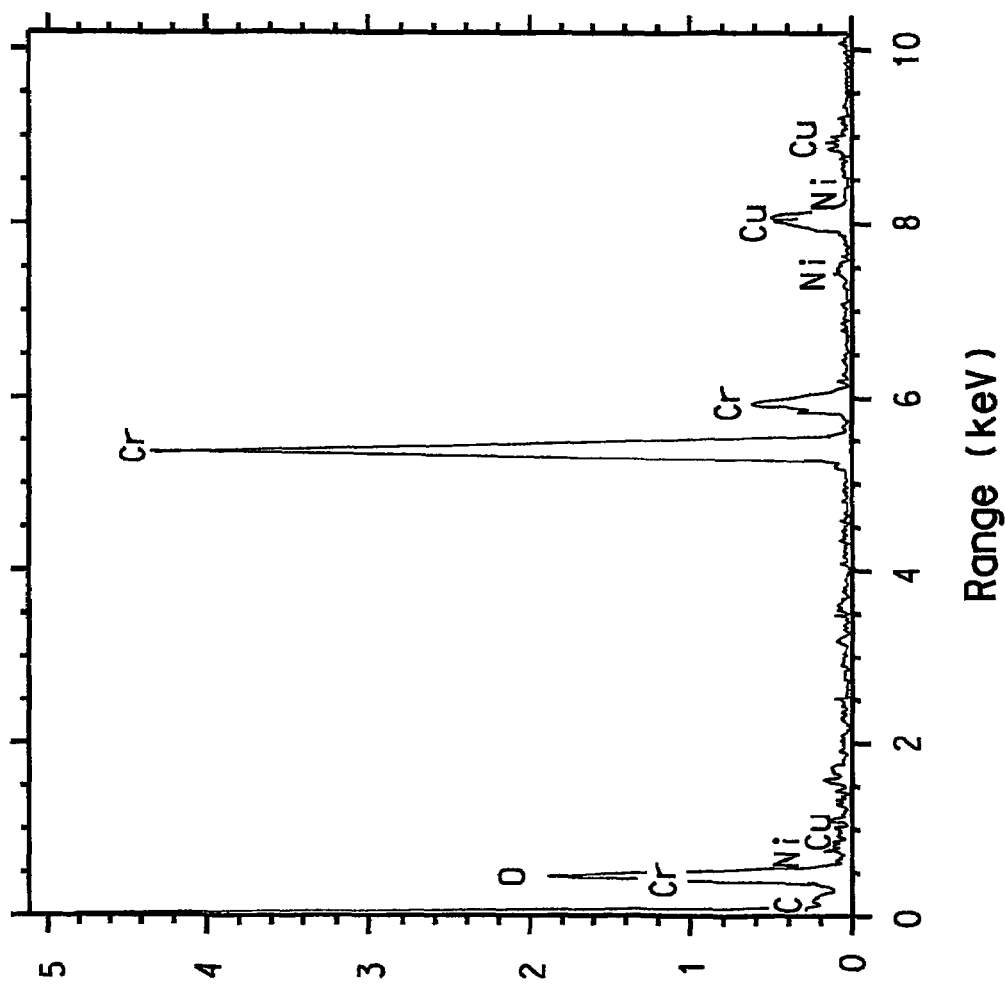
FIG. 5 represents an energy dispersive spectroscopy spectrum for a sample of nickel-substituted alpha-chromium oxide nominally containing 2 atom % nickel.

The presence of various nickel/chromium and nickel/cobalt/chromium compositions of this invention is clearly indicated by elemental analysis using EDS. FIG. 1 shows the EDS spectrum of a sample of a mixed nickel- and cobalt-substituted $\alpha$-$Cr_2O_3$ nominally containing 2 atom % nickel and 3 atom % Co. For comparison, FIG. 2 shows the EDS spectrum of $\alpha$-$Cr_2O_3$ without nickel- or cobalt-substitution. FIGS. 3 and 4 show the EDS spectrum of commercially available nickel chromite, $NiCr_2O_4$, and cobalt chromite, $CoCr_2O_4$, respectively. FIG. 5 shows the EDS spectrum of a sample of a nickel-substituted $\alpha$-$Cr_2O_3$ nominally containing 2 atom % nickel. In each of these five figures, X-ray intensity, I, representing thousands of counts is plotted against energy level, E, representing thousands of electron volts (keV). Peaks in each plot correlate with the presence of certain elements.

The presence of nickel and cobalt are clearly indicated in the EDS spectrum in FIG. 1, and the presence of nickel (but not cobalt) is clearly indicated in FIG. 5, while the nickel and cobalt peaks are absent in FIG. 2. The relative heights of 2:1 for the K$\alpha$ peaks of Cr (atomic mass 52) and Ni (atomic masses 58 and 60), respectively, in FIG. 3, and the relative heights of 2:1 for the K$\alpha$ peaks of Cr and Co (atomic mass 59) in FIG. 4, indicate that the EDS data are valid on a quantitative basis.

XAS and XRD data were obtained for a composition that was nominally 100% Cr (no cobalt added), for a composition that was nominally 95% Cr, 3% Co, and 2% Ni, for a composition that was nominally 98% Cr and 2% Ni, and for a composition that was nominally 95% Cr and 5% Ni. XAS and XRD analysis clearly show that the cobalt and nickel are substituted into $\alpha$-$Cr_2O_3$.

XRD results for a composition that is nominally 2 atom % nickel, 3 atom % cobalt, and 95 atom % chromium are shown Table 1. Diffraction peaks having d-spacings of 3.1176, 1.9144, 1.3559, 1.2440, and 1.1076 are due to a silicon internal standard added to the sample for calibration of the diffractometer. All other diffraction peaks can be indexed to the α-$Cr_2O_3$ structure with a slightly reduced unit cell volume.

XRD results for a composition that is nominally 2 atom % nickel and 98 atom % chromium are shown Table 2. Diffraction peaks having d-spacings of 3.1336, 1.92, 1.6375, 1.3579, 1.246, and 1.1085 are due to a silicon internal standard added to the sample for calibration of the diffractometer. All other diffraction peaks can be indexed to the α-$Cr_2O_3$ structure with a slightly expanded unit cell volume.

TABLE 1

XRD Results for a Ni- and Co-Substituted alpha-$Cr_2O_3$ Composition that is Nominally 95 atom % Cr, 2 atom % Ni, and 3 atom % Co

| d (Angstroms) | Height | FWHM[a] |
|---|---|---|
| 3.6002 | 88 | 0.518 |
| 3.1176 | 2932 | 0.173 |
| 2.6432 | 219 | 0.522 |
| 2.4634 | 427 | 0.404 |
| 2.2513 | 34 | 0.320 |
| 2.1631 | 178 | 0.440 |
| 1.9144 | 2767 | 0.200 |
| 1.8075 | 134 | 0.543 |
| 1.6621 | 555 | 0.569 |
| 1.6336 | 1672 | 0.235 |
| 1.4571 | 110 | 0.525 |
| 1.4243 | 256 | 0.594 |
| 1.3559 | 474 | 0.256 |
| 1.2907 | 93 | 0.669 |
| 1.2440 | 907 | 0.261 |
| 1.2059 | 44 | 0.400 |
| 1.1452 | 54 | 0.412 |
| 1.1209 | 42 | 0.369 |
| 1.1076 | 1285 | 0.236 |

[a]FWHM is full width at half maximum.

TABLE 2

XRD Results for a Ni-Substituted alpha-$Cr_2O_3$ Composition that is Nominally 98 atom % Cr and 2 atom % Ni

| d (Angstroms) | Height | FWHM[a] |
|---|---|---|
| 3.6216 | 222 | 0.579 |
| 3.1336 | 1910 | 0.138 |
| 2.6588 | 502 | 0.623 |
| 2.4655 | 1056 | 0.435 |
| 2.2546 | 125 | 0.355 |
| 2.1603 | 520 | 0.467 |
| 1.92 | 1971 | 0.159 |
| 1.8115 | 262 | 0.679 |
| 1.6612 | 1406 | 0.524 |
| 1.6375 | 1347 | 0.178 |
| 1.5738 | 110 | 0.482 |
| 1.4571 | 276 | 0.6 |
| 1.4566 | 250 | 0.742 |
| 1.4237 | 650 | 0.61 |
| 1.3579 | 388 | 0.157 |
| 1.2925 | 225 | 0.753 |
| 1.246 | 801 | 0.138 |
| 1.2329 | 174 | 0.689 |
| 1.2074 | 135 | 0.635 |
| 1.2025 | 139 | 0.617 |
| 1.1444 | 146 | 0.359 |
| 1.1249 | 144 | 0.554 |
| 1.1085 | 906 | 0.164 |
| 1.1057 | 392 | 0.272 |

[a]FWHM is full width at half maximum.

Figure 6:
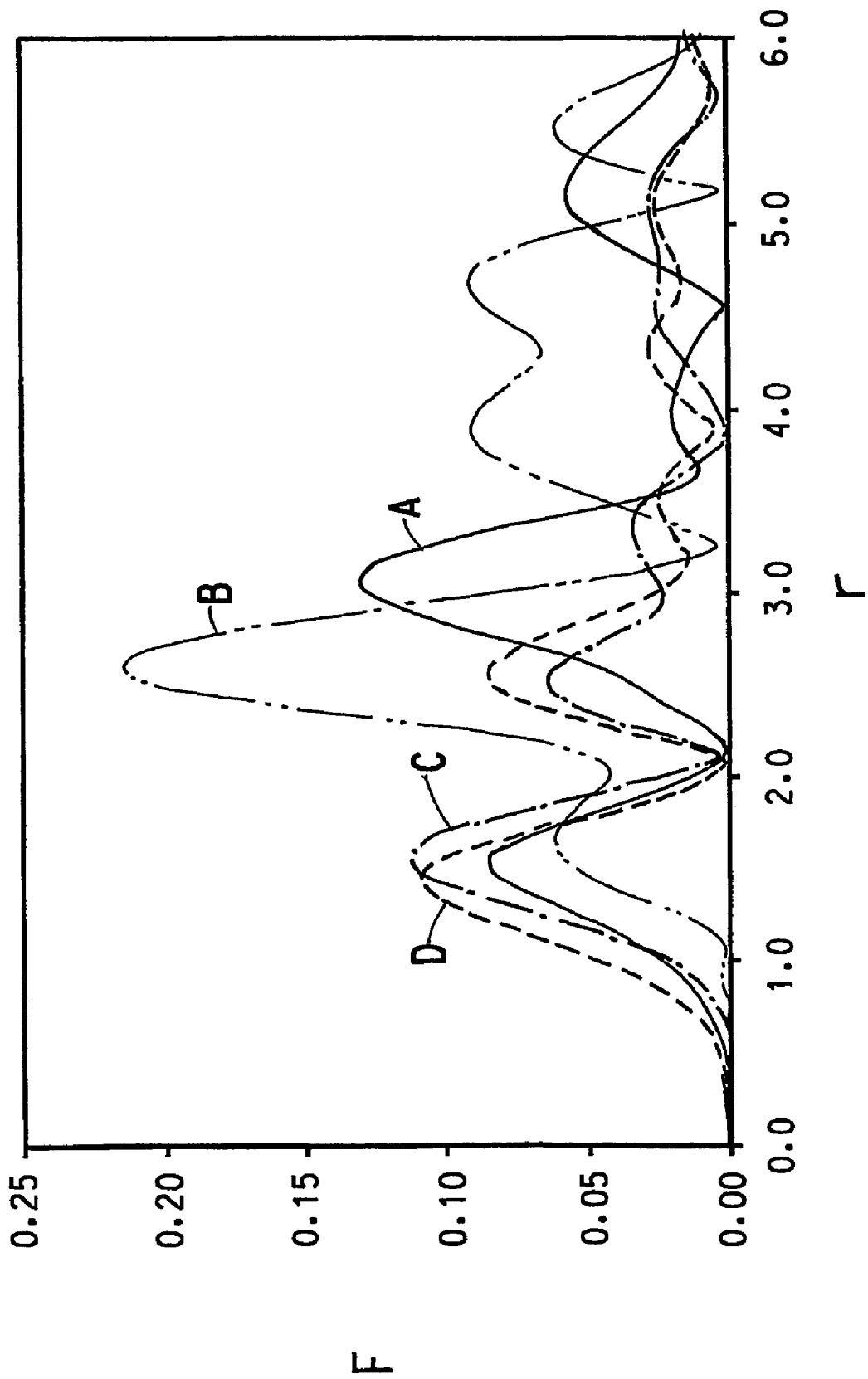
FIG. 6 represents a plot of the radial distribution function (i.e., the probability of finding an atom at a certain distance, r, from a central atom) associated with the local atomic structure around (A) a nickel central atom in NiO, (B) nickel in a sample of $NiCr_2O_4$, (C) a chromium central atoms in alpha-$Cr_2O_3$, and (D) nickel in a sample of the mixed nickel- and cobalt-substituted alpha-chromium oxide nominally containing 3 atom % cobalt and 2 atom % nickel.
Figure 7:
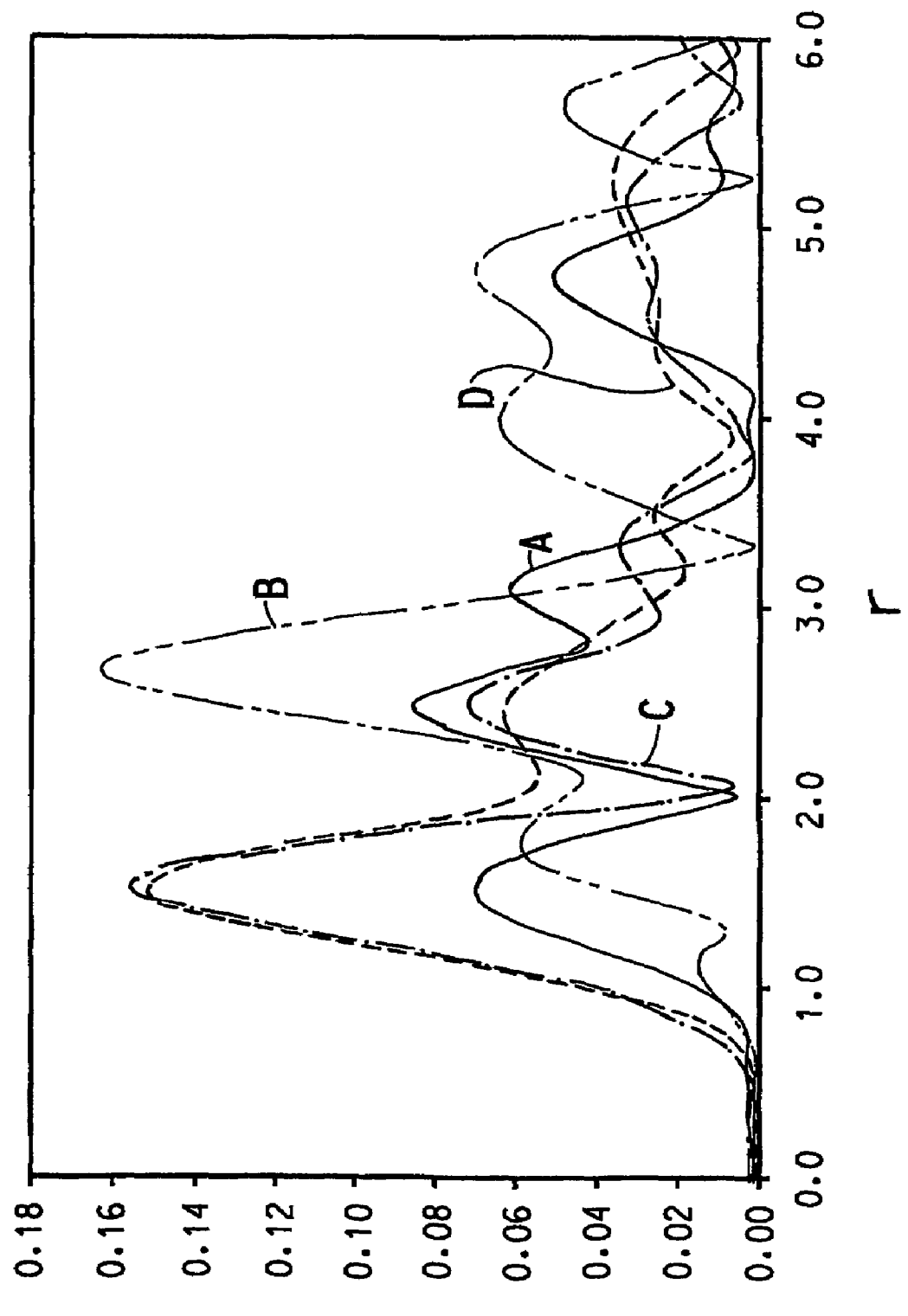
FIG. 7 represents a plot of the radial distribution function associated with the local atomic structure around (A) a cobalt central atom in CoO, (B) a cobalt central atom in $Co_3O_4$, (C) a chromium central atom in alpha-$Cr_2O_3$, and (D) a cobalt atom in a sample of the mixed nickel- and cobalt-substituted alpha-chromium oxide nominally containing 3 atom % cobalt and 2 atom % nickel.
Figure 8:
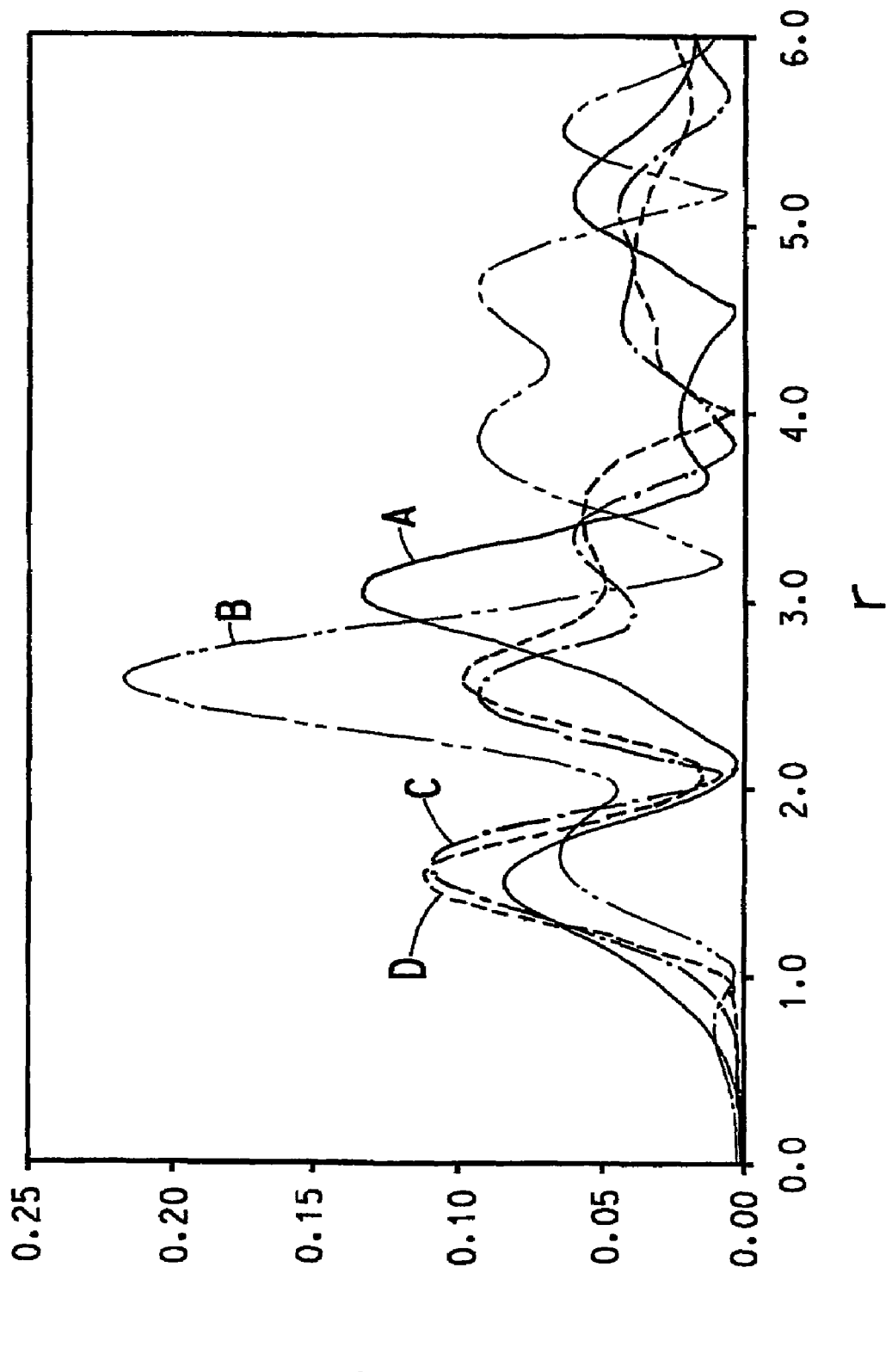
FIG. 8 represents a plot of the radial distribution function associated with the local atomic structure around (A) a nickel central atom in NiO, (B) nickel in a sample of $NiCr_2O_4$, (C) a chromium central atom in alpha-$Cr_2O_3$, and (D) a nickel atom in a sample of nickel-substituted alpha-chromium oxide nominally containing 2 atom % nickel.

FIGS. 6, 7, and 8 show the radial distribution function (RDF) for several materials. The radial distribution function represents the probability of finding an atom a certain distance, r, from a central atom. These probabilities are weighted by factors that depend on the type of atom. Thus an RDF is a representation of local atomic structure around the central atom. An RDF is obtained by Fourier transform of the extended x-ray absorption fine structure (EXAFS) data, and may be represented by a plot of the dimensionless Fourier transform magnitude, F, versus the pair separation distance in angstroms. In simplified terms, one might view a peak in an RDF plot as indicative of a distance at which there is a coordination sphere around the central atom. A small difference is expected between the actual separation distance and the "r" shown in a plot when no correction is made to account for the phase shift on backscattering of excited electrons.

In FIG. 6, F is plotted against the pair separation distance, r (shown in angstroms, uncorrected for phase shift) for each of four materials. Included in FIG. 6 are curve (A) representing the local structure around nickel in NiO, curve (B) representing the local structure around nickel in $NiCr_2O_4$, curve (C) representing the local structure around chromium in alpha-$Cr_2O_3$, and curve (D) representing the local structure around nickel in a sample of a mixed nickel- and cobalt-substituted alpha-chromium oxide nominally containing 3 atom % cobalt and 2 atom % nickel. No spinel phase was detected by electron microscopy in this sample, so all the Ni and Co are considered to be associated with the α-$Cr_2O_3$ phase, either as a separate metal oxide coating, or as a substitute for Cr in the alpha-$Cr_2O_3$ lattice.

In FIG. 7, F is plotted against the pair separation distance, r (shown in angstroms, uncorrected for phase shift) for each of four materials. Included in FIG. 7 are curve (A) representing the local structure around cobalt in CoO, curve (B) representing the local structure around cobalt in $Co_3O_4$, curve (C) representing the local structure around chromium in alpha-$Cr_2O_3$, and curve (D) representing the local structure around cobalt in the same sample of mixed nickel- and cobalt-substituted alpha-chromium oxide shown in FIG. 6 (nominally containing 3 atom % cobalt and 2 atom % nickel).

In FIG. 8, F is plotted against the pair separation distance, r (shown in angstroms, uncorrected for phase shift) for each of the four materials. Included in FIG. 8 are curve (A) representing the local structure around nickel in NiO, curve (B) representing the local structure around nickel in $NiCr_2O_4$, curve (C) representing the local structure around chromium in alpha-$Cr_2O_3$, and curve (D) representing the local structure around nickel in a sample of nickel-substituted alpha-chromium oxide nominally containing 2 atom % nickel. No spinel phase was detected by electron microscopy in this sample, so all the Ni is considered to be associated with the alpha-$Cr_2O_3$ phase, either as a separate metal oxide coating, or as a substitute for Cr in the alpha-$Cr_2O_3$ lattice.

The curve in FIG. 6 representing the local structure around nickel in the mixed nickel- and cobalt-substituted alpha-chromium oxide and the curve in FIG. 7 representing the local structure around cobalt in the same composition, indicate that the local atomic structure around Ni and Co in this sample bears no resemblance to that of expected common nickel and cobalt oxide phases, but is very similar to that of Cr in the α-$Cr_2O_3$ phase. A similar conclusion may be drawn by comparison of the curves in FIG. 8; namely, that the local atomic structure around Ni in the Cr/Ni 98/2 sample bears no resemblance to that of expected common nickel oxide phase, but is very similar to that of Cr in the α-$Cr_2O_3$ phase.

Table 3 gives the unit cell parameters and the unit cell volume for unsubstituted alpha-chromium oxde as well as three substituted alpha-chromium oxide compositions. The change in unit cell volume may be understood in terms of differences in the ionic radii of the substituted metals. According to data presented by Shannon and Prewitt in *Acta Crystallographica*, Volume B25, pages 925 to 945 (1969), the ionic radii of high spin $Cr^{+3}$, low spin $Co^{+3}$, low spin $Ni^{+3}$, high spin $Ni^{+3}$, and $Ni^{+2}$ are 62 pm, 53 pm, 56 pm, 60 pm, and 69 pm, respectively. As discussed in co-pending U.S. patent application CL-2099, substitution of $Co^{+3}$ for $Cr^{+3}$ in the $\alpha$-$Cr_2O_3$ lattice results in a slight contraction of the unit cell. In the case of the present invention where nickel or both nickel and cobalt are substituted into the $\alpha$-$Cr_2O_3$ lattice, the unit cell may expand or contract depending on the oxidation state and spin state of nickel and whether cobalt is present or not.

TABLE 3

Characterization of Metal-Substituted alpha-Chromium(III) Oxides

| Cr/Co/Ni Composition atom % | Lattice parameters | | Unit Cell Volume ($nm^3$) |
|---|---|---|---|
| | a, nm | c, nm | |
| Cr100% | 0.49321 | 1.35207 | 0.284839 |
| Cr95%/Co3%/Ni2% | 0.49292 | 1.35127 | 0.284332 |
| Cr98%/Ni2% | 0.49378 | 1.35327 | 0.285743 |
| Cr95%/Ni5% | 0.49371 | 1.35358 | 0.285743 |

[a]Estimated in error in a, c, and unit cell volume are 0.00001 nm, 0.00002 nm, and 0.000013 $nm^3$, respectively.

Results for cobalt-substituted alpha-chromium oxide compositions disclosed in co-pending U.S. patent application Ser. No. 60/405,220 [CL2099 US PRV], filed Aug. 22, 2002, indicate the solubility limit for cobalt in the $\alpha$-$Cr_2O_3$ phase is about 6 atom %. XAS and XRD data for the nickel-substituted alpha-chromium oxide compositions nominally containing 2% nickel and 5% nickel indicate that the solubility limit for nickel in the $\alpha$-$Cr_2O_3$ lattice is about 2 atom % (see Preparation Examples 7 and 8).

Other phases such as chromium-nickel and chromium-cobalt spinel phases may be present in the chromium oxide compositions of the present invention particularly at higher loadings of cobalt or nickel. The presence of these phases is detected by EDS, TEM, and XAS.

The surface area of the chromium oxide compositions of the present invention is typically in the range of about 1 to 100 m2/gram. The $\alpha$-$Ni_xCo_yCr_{2-x-y}O_3$ phase present in the compositions prepared by the process of this invention is typically made up of crystallites having particle sizes varying from about 20 to about 400 nm, typically from about 40 to about 250 nm. Included in this invention are microcrystalline materials with particle sizes smaller than 20 nm.

The calcined chromium oxide compositions of the present invention may be formed into various shapes such as pellets, granules, and extrudates for use in packing reactors. They may also be used in powder form.

The compositions of this invention may further comprise one or more additives in the form of metal compounds that alter the selectivity or activity of the crystalline nickel-substituted or crystalline mixed nickel- and cobalt-substituted alpha-chromium oxides or the fluorinated substituted alpha-chromium oxides. Suitable additives may be selected from the group consisting of fluorides, oxides, or oxyfluoride compounds of Mg, Ca, Sc, Y, La, Ti, Zr, Hf, V, Nb, Ta, Mo, W, Mn, Re, Fe, Ru, Co, Rh, Ir, Ni, Pd, Pt, Cu, Ag, Au, Ce, and Zn.

The total content of the additive(s) in the compositions of the present invention may be from about 0.05 atom % to about 15 atom % based on the total metal content of the compositions. The additives may be incorporated into the compositions of the present invention by standard procedures such as by impregnation.

Typically, the calcined compositions will be pre-treated with a fluorinating agent prior to use as catalysts for changing the fluorine content of halogenated hydrocarbon compounds. Typically this fluorinating agent is HF though other materials may be used such sulfur tetrafluoride, carbonyl fluoride, and fluorinated hydrocarbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 hours at a temperature of, for example, about 200° C. to about 450° C. Nevertheless, this pre-treatment is not essential.

As noted above, catalysts provided in accordance with this invention may be used to change the fluorine distribution in hydrocarbons and/or halogenated hydrocarbons. The fluorine distribution in a hydrocarbon or a halogenated hydrocarbon may be changed by increasing the fluorine content of the hydrocarbon or halogenated hydrocarbon. The fluorine distribution of a halogenated hydrocarbon may also be changed by decreasing the fluorine content of the halogenated hydrocarbon, and/or rearranging the placement of fluorine atoms on the carbon atoms of the halogenated hydrocarbon. Of note are processes where the fluorine distribution in halogenated hydrocarbons containing from one to twelve carbon atoms is changed, particularly processes where the fluorine distribution in halogenated hydrocarbons containing one to six carbon atoms is changed. Also of note are processes where the fluorine content of hydrocarbons containing from one to twelve carbon atoms is increased, particularly processes where the fluorine content in hydrocarbons containing one to six carbon atoms is increased. Processes for changing the fluorine distribution in halogenated hydrocarbons include fluorination, chlorofluorination, isomerization, disproportionation, dehydrofluorination, and chlorodefluorination. Processes for increasing the fluorine content of hydrocarbons include fluorination and chlorofluorination. The processes of this invention are characterized by using as the catalyst a composition comprising at least one chromium-containing component selected from the group consisting of the crystalline nickel-substituted alpha-chromium oxide, crystalline mixed nickel- and cobalt-substituted alpha-chromium oxide as described above, and said substituted alpha-chromium oxide which has been treated with a fluorinating agent. Typical of saturated halogenated hydrocarbons suitable for fluorination, chlorofluorination, isomerization, disproportionation, dehydrofluorination, and chlorodefluorination processes are those which have the formula $C_nH_aBr_bCl_cF_d$, wherein n is an integer from 1 to 6, a is an integer from 0 to to 12, b is an integer from 0 to 4, c is an integer from 0 to 13, and d is an integer from 0 to 13, the sum of b, c, and d is at least 1, and that the sum of a, b, c, and d is equal to 2n+2, provided that n is at least 2 for isomerization, disproportionation, and dehydrofluorination processes, a is at least one for dehydrofluorination processes, b is 0 for chlorodefluorination processes, b+c is at least 1 for fluorination processes and is 0 for dehydrofluorination processes, a+b+c is at least 1 for fluorination, chlorodefluorination, isomerization, disproportionation, and dehydrofluorination processes, and d is at least 1 for isomerization, disproportionation, dehydrofluorination, and chlorodefluorination processes. Typical of unsaturated halogenated hydrocarbons suitable for fluorination, chlorofluorination, isomerization, disproportionation, and chlorodefluorination processes are those which have the formula $C_pH_eBr_fCl_gF_h$, wherein p is an integer from 2 to 6, e is an integer from 0 to to 10, f is an integer from 0 to 2, g is an integer from 0 to 12, and h is an integer from 0 to 11, the sum of f, g, and h is at least 1, and that the sum of e, f, g, and h is equal to 2p, provided that f is 0 for chlorodefluorination processes, e+f+g is at least 1 for isomerization and disproportionation processes, and h is at least 1 for isomerization, disproportionation, and chlorodefluorination processes. Typical of saturated hydrocarbons suitable for chlorofluorination are those which have the formula $C_qH_r$, where q is an integer from 1 to 6 and r is 2q+2. Typical of unsaturated hydrocarbons suitable for fluorination and chlorofluorination are those which have the formula $C_iH_j$ where i is an integer from 2 to 6 and j is 2i.

Fluorination

Included in this invention is a process for increasing the fluorine content of a halogenated hydrocarbon or an unsaturated hydrocarbon compound by reacting said compound(s) with hydrogen fluoride in the vapor phase in the presence of a catalyst composition comprising at least one chromium-containing component selected from the group consisting of the crystalline nickel-substituted alpha-chromium oxide or crystalline mixed nickel- and cobalt-substituted alpha-chromium oxide described above, and said substituted alpha-chromium oxide which has been treated with a fluorinating agent. The catalyst composition may optionally contain additional components such as additives to alter the activity and selectivity of the catalyst.

Halogenated hydrocarbon compounds suitable as starting materials for the fluorination process of this invention may be saturated or unsaturated. Saturated halogenated hydrocarbon compounds suitable for the fluorination process of this invention include those of the general formula $C_nH_aBr_bCl_cF_d$, wherein n is an integer from 1 to 6, a is an integer from 0 to 12, b is an integer from 0 to 4, c is an integer from 0 to 13, and d is an integer from 0 to 13, and the sum of a, b, c, and d is equal to 2n+2, provided that b or c is at least 1. Unsaturated halogenated hydrocarbon compounds suitable for the process of this invention are given by the general formula $C_pH_eBr_fCl_gF_h$, wherein p is an integer from 2 to 6, e is an integer from 0 to to 10, f is an integer from 0 to 2, g is an integer from 0 to 12, and h is an integer from 0 to 11, the sum of f, g, and h is at least 1 and the sum of e, f, g, and h is equal to 2p. Unsaturated hydrocarbons suitable for fluorination are those which have the formula CiHj where i is an integer from 2 to 6 and j is 2i. The fluorine content of saturated compounds of the formula $C_nH_aBr_bCl_cF_d$, unsaturated compounds of the formula $C_pH_eBr_fCl_gF_h$ and/or unsaturated compounds of the formula $C_iH_j$ may be increased by reacting said compounds with HF in the vapor phase in the presence of a catalyst composition comprising at least one chromium-containing component selected from the group consisting of the crystalline nickel-substituted alpha-chromium oxide described above, the crystalline mixed nickel- and cobalt-substituted alpha-chromium oxide described above, and said substituted alpha-chromium oxide which has been treated with a fluorinating agent. Such a process is referred to herein as a vapor phase fluorination reaction.

The vapor phase fluorination reactions are typically conducted at temperatures of from about 150° C. to 500° C. For saturated compounds the fluorination is preferably carried out from about 175° C. to 400° C. and more preferably from about 200° C. to about 350° C. For unsaturated compounds the fluorination is preferably carried out from about 150° C. to 350° C. and more preferably from about 175° C. to about 300° C.

The vapor phase fluorination reactions are typically conducted at atmospheric and superatmospheric pressures. For reasons of convenience in downstream separations processes (e.g., distillation), pressures of up to about 30 atmospheres may be employed.

The vapor phase fluorination reactions are typically conducted in a tubular reactor. The reactor and its associated feed lines, effluent lines, and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

The contact time in the reactor is typically from about 1 to about 120 seconds and preferably from about 5 to about 60 seconds.

The amount of HF reacted with the unsaturated hydrocarbons or halogenated hydrocarbon compounds should be at least a stoichiometric amount. The stoichiometric amount is based on the number of Br and/or Cl substituents to be replaced by F in addition to one mole of HF to saturate the carbon-carbon double bond if present. Typically, the molar ratio of HF to the said compounds of the formulas $C_nH_aBr_bCl_cF_d$, $C_pH_eBr_fCl_gF_h$, and $C_iH_j$ can range from about 0.5:1 to about 100:1, preferably from about 2:1 to about 50:1, and more preferably from about 3:1 to about 20:1. In general, with a given catalyst composition, the higher the temperature and the longer the contact time, the greater is the conversion to fluorinated products. The above variables can be balanced, one against the other, so that the formation of higher fluorine substituted products is maximized.

Examples of saturated compounds of the formula $C_nH_aBr_bCl_cF_d$ which may be reacted with HF in the presence of the catalyst of this invention include $CH_2Cl_2$, $CH_2Br_2$, $CHCl_3$, $CCl_4$, $C_2Cl_6$, $C_2BrCl_5$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_2HBrF_4$, $C_2H_2Cl_4$, $C_2H_2Cl_3F$, $C_2H_2Cl_2F_2$, $C_2H_2ClF_3$, $C_2H_3Cl_3$, $C_2H_3Cl_2F$, $C_2H_3ClF_2$, $C_2H_4Cl_2$, $C_2H_4ClF$, $C_3Cl_6F_2$, $C_3Cl_5F_3$, $C_3Cl_4F_4$, $C_3Cl_3F_5$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_6$, $C_3H_2BrCl_5$, $C_3H_2Cl_5F$, $C_3H_2Cl_4F_2$, $C_3H_2Cl_3F_3$, $C_3H_2Cl_2F_4$, $C_3H_2ClF_5$, $C_3H_3Cl_5$, $C_3H_3Cl_4F$, $C_3H_3Cl_3F_2$, $C_3H_3Cl_2F_3$, $C_3H_3ClF_4$, $C_3H_4Cl_4$, $C_4Cl_4Cl_4$, $C_4Cl_4Cl_6$, $C_4H_5Cl_5$, $C_4H_5Cl_4F$, and $C_5H_4Cl_8$.

Specific examples of fluorination reactions of saturated halogenated hydrocarbon compounds which may be carried out under the conditions described above using the catalysts of, this invention include the conversion of $CH_2Cl_2$ to $CH_2F_2$, the conversion of $CHCl_3$ to a mixture of $CHCl_2F$, $CHClF_2$, and $CHF_3$, the conversion of $CH_3CHCl_2$ to a mixture of $CH_3CHClF$ and $CH_3CHF_2$, the conversion of $CH_2ClCH_2Cl$ to a mixture of $CH_3CHClF$ and $CH_3CHF_2$, the conversion of $CH_3CCl_3$ to a mixture of $CH_3CCl_2F$, $CH_3CClF_2$, and $CH_3CF_3$, the conversion of $CH_2ClCF_3$ to $CH_2FCF_3$, the conversion of $CHCl_2CF_3$ to a mixture of $CHClFCF_3$ and $CHF_2CF_3$, the conversion of $CHClFCF_3$ to $CHF_2CF_3$, the conversion of $CHBrFCF_3$ to $CHF_2CF_3$, the conversion of $CCl_3CF_2CCl_3$ to a mixture of $CCl_2FCF_2CClF_2$ and $CClF_2CF_2CClF_2$, the conversion of $CCl_3CH_2CCl_3$ to $CF_3CH_2CF_3$, the conversion of $CCl_3CH_2CHCl_2$ to a mixture of $CF_3CH_2CHF_2$, $CF_3CH=CHCl$, and $CF_3CH=CHF$, the conversion of $CF_3CCl_2CClF_2$ to a mixture of $CF_3CCl_2CF_3$, and $CF_3ClFCF_3$, the conversion of $CF_3CCl_2CF_3$ to $CF_3ClFCF_3$, and the conversion of a mixture comprising $CF_3CF_2CHCl_2$ and $CClF_2CF_2CHClF$ to a mixture of $CF_3CF_2CHClF$ and $CF_3CF_2CHF_2$.

Examples of unsaturated compounds of the formula $C_pH_eBr_fCl_gF_h$ and $C_iH_j$ which may be reacted with HF in the presence of the catalysts of this invention include $C_2Cl_4$, $C_2BrCl_3$, $C_2Cl_3F$, $C_2Cl_2F_2$, $C_2ClF_3$, $C_2F_4$, $C_2HCl_3$, $C_2HBrCl_2$, $C_2HCl_2F$, $C_2HClF_2$, $C_2HF_3$, $C_2H_2Cl_2$, $C_2H_2ClF$, $C_2H_2F_2$, $C_2H_3Cl$, $C_2H_3F$, $C_2H_4$, $C_3H_6$, $C_3H_5Cl$, $C_3H_4Cl_2$, $C_3H_3Cl_3$, $C_3H_2Cl_4$, $C_3HCl_5$, $C_3Cl_6$, $C_3Cl_5F$, $C_3Cl_4F_2$, $C_3Cl_3F_3$, $C_3Cl_2F_4$, $C_3ClF_5$, $C_3HF_5$, $C_3H_2F_4$, $C_3F_6$, $C_4Cl_8$, $C_4Cl_2F_6$, $C_4ClF_7$, $C_4H_2F_6$, and $C_4HClF_6$.

Specific examples of fluorination reactions of unsaturated halogenated hydrocarbon compounds which may be carried out using the catalysts of this invention include the conversion of $CHCl=CCl_2$ to a mixture of $CH_2ClCF_3$ and $CH_2FCF_3$, the conversion of $CCl_2=CCl_2$ to a mixture of $CHCl_2CF_3$, $CHClFCF_3$, and $CHF_2CF_3$, the conversion of $CCl_2=CH_2$ to a mixture of $CH_3CCl_2F$, $CH_3CClF_2$, and $CH_3CF_3$, the conversion of $CH_2=CHCl$ to a mixture of $CH_3CHClF$ and $CH_3CHF_2$, the conversion of $CF_2=CH_2$ to $CH_3CF_3$, the conversion of $CCl_2=CClCF_3$ to a mixture of $CF_3CHClCClF_2$, $CF_3CHClCF_3$, and/or $CF_3CCl=CF_2$, the conversion of $CF_3CF=CF_2$ to $CF_3CHFCF_3$, the conversion of $CF_3CH=CF_2$ to $CF_3CH_2CF_3$, and the conversion of $CF_3CH=CHF$ to $CF_3CH_2CHF_2$.

Mixtures of saturated halogenated hydrocarbon compounds or mixtures of unsaturated hydrocarbons and/or halogenated hydrocarbon compounds may also be used in the vapor phase fluorination reactions as well as mixtures comprising both unsaturated hydrocarbons and halogenated hydrocarbon compounds. Specific examples of mixtures of saturated halogenated hydrocarbon compounds and mixtures of unsaturated hydrocarbons and unsaturated halogenated hydrocarbon compounds that may be subjected to vapor phase fluorination using the catalysts of this invention include a mixture of $CH_2Cl_2$ and $CCl_2=CCl_2$, a mixture of $CCl_2FCClF_2$ and $CCl_3CF_3$, a mixture of $CCl_2=CCl_2$ and $CCl_2=CClCCl_3$, a mixture of $CH_2=CHCH_3$ and $CH_2=CClCH_3$, a mixture of $CH_2Cl_2$ and $CH_3CCl_3$, a mixture of $CHF_2CClF_2$ and $CHClFCF_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHCl_2CH_2CCl_3$ and $CCl_3CH_2CCl_3$, a mixture of and $CF_3CH_2CCl_2F$ and $CF_3CH=CCl_2$, and a mixture of $CF_3CH=CHCl$ and $CF_3CH=CCl_2$.

Chlorofluorination

Included in this invention is a process for increasing the fluorine content of a hydrocarbon compound or a halogenated hydrocarbon compound by reacting said compound with hydrogen fluoride (HF) and chlorine (Cl2) in the vapor phase in the presence of a catalyst composition comprising at least one chromium-containing component selected from the group consisting of the crystalline nickel-substituted alpha-chromium oxide described above, the crystalline mixed nickel- and cobalt-substituted alpha-chromium oxide described above, and said substituted alpha-chromium oxide which has been treated with a fluorinating agent. The catalyst composition may optionally contain additional components such as another catalytically effective metal.

Halogenated hydrocarbon compounds suitable as starting materials for the chlorofluorination process of this invention may be saturated or unsaturated. Saturated halogenated hydrocarbon compounds suitable for the fluorination process of this invention include those of the general formula $C_nH_aBr_bCl_cF_d$, wherein n is an integer from 1 to 6, a is an integer from 0 to 12, b is an integer from 0 to 4, c is an integer from 0 to 13, and d is an integer from 0 to 13, the sum of b, c, and d is at least 1, and the sum of a, b, c, and d is equal to 2n+2, provided that a+b+c is at least 1. Preferred chlorofluorination processes include those involving said saturated starting materials where a is at least 1. Saturated hydrocarbon compounds suitable for chlorofluorination are those which have the formula $C_qH_r$, where q is an integer from 1 to 6 and r is 2q+2. Unsaturated halogenated hydrocarbon compounds suitable for the chlorofluorination processes of this invention include those of the general formula $C_pH_eBr_fCl_gF_h$, wherein p is an integer from 2 to 6, e is an integer from 0 to 10, f is an integer from 0 to 2, g is an integer from 0 to 12, and h is an integer from 0 to 11, the sum of f, g, and h is at least 1 and the sum of e, f, g, and h is equal to 2p. Unsaturated hydrocarbon compounds suitable for fluorination are those which have the formula $C_iH_j$ where i is an integer from 2 to 6 and j is 2i. The fluorine content of saturated compounds of the formulas $C_nH_aBr_bCl_cF_d$ and $C_qH_r$, and/or unsaturated compounds of the formulas $C_pH_eBr_fCl_gF_h$ and $C_iH_j$ may be increased by reacting said compounds with HF and $Cl_2$ in the vapor phase in the presence of a catalyst composition comprising at least one chromium-containing component selected from the group consisting of the crystalline nickel-substituted alpha-chromium oxide described above, the crystalline mixed nickel- and cobalt-substituted alpha-chromium oxide described above, and said substituted alpha-chromium oxide which has been treated with a fluorinating agent. Such a process is referred to herein as a vapor phase chlorofluorination reaction.

The conditions of the vapor phase chlorofluorination reactions are similar to those described above for vapor phase fluorination reactions in terms of the temperature ranges, contact times, pressures, and mole ratios of HF to the halogenated hydrocarbon compounds. The amount of chlorine ($Cl_2$) fed to the reactor is based on whether the halogenated hydrocarbon compounds fed to the reactor is unsaturated and the number of hydrogens in $C_nH_aBr_bCl_cF_d$, $C_qH_r$, $C_pH_eBr_fCl_gF_h$, and $C_iH_j$ that are to be replaced by chlorine and fluorine. One mole of $Cl_2$ is required to saturate a carbon-carbon double bond and a mole of $Cl_2$ is required for every hydrogen to be replaced by chlorine or fluorine. A slight excess of chlorine over the stoichiometric amount may be necessary for practical reasons, but large excesses of chlorine will result in complete chlorofluorination of the products. The ratio of $Cl_2$ to halogenated hydrocarbon compound is typically from about 1:1 to about 10:1.

Specific examples of vapor phase chlorofluorination reactions of saturated halogenated hydrocarbon compounds of the general formula $C_nH_aBr_bCl_cF_d$ and saturated hydrocarbon compounds of the general formula $C_qH_r$ which may be carried out using the catalysts of this invention include the conversion of $C_2H_6$ to a mixture containing $CH_2ClCF_3$, the conversion of $CH_2ClCF_3$ to a mixture of $CHClFCF_3$ and $CHF_2CF_3$, the conversion of $CCl_3CH_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CHCl_2$ to a mixture of $CF_3CCl_2CClF_2$, $CF_3CCl_2CF_3$, $CF_3CClFCClF_2$, and $CF_3CClFCF_3$, the conversion of $CCl_3CHClCH_2Cl$ to a mixture of $CF_3CCl_2CClF_2$, $CF_3CCl_2CF_3$, $CF_3CClFCClF_2$, and $CF_3CClFCF_3$, the conversion of $CHCl_2CCl_2CH_2Cl$ to a mixture of $CF_3CCl_2CClF_2$, $CF_3CCl_2CF_3$, $CF_3CClFCClF_2$, and $CF_3CClFCF_3$, the conversion of $CCl_3CH_2CH_2Cl$ to a mixture of $CF_3CCl_2CHF_2$, $CF_3CClFCHF_2$, $CF_3CClFCClF_2$, and $CF_3CCl_2CF_3$, and the conversion of $CCl_3CH_2CHCl_2$ to a mixture of $CF_3CCl_2CHF_2$, $CF_3CClFCHF_2$, $CF_3CClFCClF_2$, and $CF_3CCl_2CF_3$.

Specific examples of vapor phase chlorofluorination reactions of unsaturated halogenated hydrocarbon compounds of the general formula $C_pH_eBr_fCl_gF_h$ and unsaturated hydrocarbon compounds of the general formula $C_iH_j$ which may be carried out using the catalysts of this invention include the conversion of $C_2H_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, the conversion of $C_2Cl_4$ to a mixture of $CCl_3CClF_2$, $CCl_2FCCl_2F$, $CClF_2CCl_2F$, $CCl_3CF_3$, $CF_3CCl_2F$, and $CClF_2CClF_2$, and the conversion of $C_3H_6$ or $CF_3CCl=CCl_2$ to a mixture of $CF_3CCl_2CClF_2$, $CF_3CCl_2CF_3$, $CF_3CClFCClF_2$, and $CF_3CClFCF_3$.

Of note is a catalytic process for producing a mixture of 1,2,2-trichloro-1,1,3,3,3-pentafluoropropane (i.e., $CClF_2CCl_2CF_3$ or CFC-215aa), 2,2-dichloro-1,1,1,3,3,3-hexafluoropropane (i.e., $CF_3CCl_2CF_3$ or CFC-216aa), 1,2-dichloro-1,1,1,3,3,3-hexafluoropropane (i.e., $CClF_2CClFCF_3$ or CFC-216ba), and 2-chloro-1,1,1,2,3,3,3-heptafluoropropane (i.e., $CF_3CClFCF_3$ or CFC-217ba), by the chlorofluorination of a hexahalopropene of the formula $C_3Cl_{6-x}F_x$, wherein x equals 0 to 4. Preferred hexahalopropenes of the formula $C_3Cl_{6-x}F_x$ include 1,2,2-trichloro-3,3,3-trifluoro-1-propene (i.e., $CCl_2=CClCF_3$ or CFC-1213xa) and hexachloropropene (i.e., $CCl_2=CClCCl_3$). The mixture of CFC-215aa, -216aa, -216ba, and -217ba is produced by reacting the above unsaturated compounds with $Cl_2$ and HF in the vapor phase in the presence of the catalysts of this invention at temperatures from about 150° C. to about 450° C., preferably about 250° C. to 400° C.

The amount of HF fed to the reactor should be at least a stoichiometric amount based on the number of Cl substitutents in the $C_3Cl_{6-x}F_x$ starting material(s) and the desired composition of the final product. In the case of chlorofluorination of CFC-1213xa to a mixture of chlorofluoropropanes having an average number of fluorine substituents of six, the stoichiometric ratio of HF to CFC-1213xa is 3:1. Preferred ratios of HF to $C_3Cl_{6-x}F_x$ starting material(s) are typically in the range of about the stoichiometric ratio to about 30:1, more preferably from about 8:1 to 25:1.

The amount of chlorine fed to the reactor should be at least a stoichiometric amount. Preferred molar ratios of $Cl_2$ to CFC-1213xa are from about 1:1 to about 5:1.

Preferred contact times are from about 5 seconds to about 60 seconds.

Further information on the chlorofluorination of CFC-1213xa is provided in U.S. Patent Application 60/405,222 [CL2108 US PRV] filed Aug. 22, 2002, and hereby incorporated by reference herein in its entirety.

Mixtures of saturated hydrocarbon compounds and saturated halogenated hydrocarbon compounds and mixtures of unsaturated hydrocarbon compounds and unsaturated halogenated hydrocarbon compounds as well as mixtures comprising both saturated and unsaturated compounds may be chlorofluorinated using the catalysts of the present invention. Specific examples of mixtures of saturated and unsaturated hydrocarbons and halogenated hydrocarbons that may be used include a mixture of $CCl_2=CCl_2$ and $CCl_2=CClCCl_3$, a mixture of $CHCl_2CCl_2CH_2Cl$ and $CCl_3CHClCH_2Cl$, a mixture of $CHCl_2CH_2CCl_3$ and $CCl_3CHClCH_2Cl$, a mixture of $CHCl_2CHClCCl_3$, $CCl_3CH_2CCl_3$, and $CCl_3CCl_2CH_2Cl$, a mixture of $CHF_2CH_2CF_3$ and $CHCl=CHCF_3$, and a mixture of $CH_2=CH_2$ and $CH_2=CHCH_3$.

Isomerization and Disproportionation

Included in this invention is a process for changing the fluorine distribution in a halogenated hydrocarbon compound by isomerizing said halogenated hydrocarbon compound in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent.

Also included in this invention is a process for changing the fluorine distribution in a halogenated hydrocarbon compound by disproportionating said halogenated hydrocarbon compound in the presence of a catalyst composition comprising at least one chromium-containing component selected from the group consisting of the crystalline nickel-substituted alpha-chromium oxide described above, the nickel- and cobalt-substituted alpha-chromium oxide described above, and said nickel-substituted (and optionally cobalt-substituted) alpha-chromium oxide which has been treated with a fluorinating agent.

Halogenated hydrocarbon compounds suitable as starting materials for the isomerization and disproportionation processes of this invention may be saturated or unsaturated. Saturated halogenated hydrocarbon compounds suitable for the isomerization and disproportionation processes of this invention include those of the general formula $C_nH_aBr_bCl_cF_d$, wherein n is an integer from 2 to 6, a is an integer from 0 to 12, b is an integer from 0 to 4, c is an integer from 0 to 13, and d is an integer from 1 to 13, and the sum of a, b, c, and d is equal to 2n+2, provided that a+b+c is at least 1. Unsaturated halogenated hydrocarbon compounds suitable for the isomerization and disproportionation processes of this invention include those of the general formula $C_pH_eBr_fCl_gF_h$, wherein p is an integer from 2 to 6, e is an integer from 0 to 10, f is an integer from 0 to 2, g is an integer from 0 to 12, and h is an integer from 1 to 11, and the sum of e, f, g, and h is equal to 2p, provided that the sum of e, f, and g is at least 1.

In one embodiment of the present invention, the fluorine distribution of a halogenated hydrocarbon compound is changed by rearranging the H, Br, and/or Cl substituents in the molecule (typically to a thermodynamically preferred arrangement) while maintaining the same number of H, Br, Cl, and F substituents, respectively. This process is referred to herein as isomerization.

In another embodiment of the present invention, the fluorine distribution of a halogenated hydrocarbon compound is changed by exchanging at least one F substituent of one molecule of the halogenated hydrocarbon starting material with a least one H, Br, and/or Cl substituent of another molecule of the halogenated hydrocarbon starting material so as to result in the formation of one or more halogenated hydrocarbon compounds having a decreased fluorine content compared to the halogenated hydrocarbon starting material and one or more halogenated hydrocarbon compounds having an increased fluorine content compared to the halogenated hydrocarbon starting material. This process is referred to herein as disproportionation.

In another embodiment of the present invention, said contacting of halogenated hydrocarbon compounds can result in the formation of one or more pairs of halogenated hydrocarbon compounds. In this case, one member of the pair has a larger number of H, Br, Cl, or F substituents and the other member of the pair has a lower number of H, Br, Cl, or F substituents. This process is referred to herein as disproportionation.

In another embodiment of the present invention, both isomerization and disproportionation reactions may occur simultaneously.

Whether carrying out isomerization, disproportionation, or both isomerization and disproportionation, the fluorine distribution of saturated compounds of the formula $C_nH_aBr_b\text{-}Cl_cF_d$ and/or unsaturated compounds of the formula $C_pH_eBr_f\text{-}Cl_gF_h$ may be changed in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent.

The isomerization and disproportionation reactions are typically conducted at temperatures of from about 150° C. to 500° C., preferably from about 200° C. to about 400° C. The contact time in the reactor is typically from about 1 to about 120 seconds and preferably from about 5 to about 60 seconds. The isomerization and disproportionation reactions may be carried out in the presence of an inert gas such as helium, argon, or nitrogen though this is not preferred. The isomerization and disproportionation reactions may be carried out in the presence of small amounts of HF and HCl, but this is not preferred.

Specific examples of vapor phase isomerization reactions which may be carried out using the catalysts of this invention include the conversion of $CClF_2CCl_2F$ to $CCl_3CF_3$, the conversion of $CClF_2CClF_2$ to $CF_3CCl_2F$, the conversion of $CHF_2CClF_2$ to $CF_3CHClF$, the conversion of $CHF_2CHF_2$ to $CF_3CH_2F$, the conversion of $CF_3CClFCClF_2$ to $CF_3CCl_2CF_3$, and the conversion of $CF_3CHFCHF_2$ to $CF_3CH_2CF_3$.

Specific examples of vapor phase disproportionation reactions which may be carried out using the catalysts of this invention include the conversion of $CClF_2CClF_2$ to a mixture of $CClF_2CCl_2F$, $CCl_3CF_3$, and $CF_3CClF_2$ and the conversion of of $CHClFCF_3$ to a mixture of $CHCl_2CF_3$, and $CHF_2CF_3$.

Of note is a process for the conversion of a mixture of 2-chloro-1,1,2,2-tetrafluoroethane (i.e., $CHF_2CClF_2$ or HCFC-124a) and 2-chloro-1,1,1,2-tetrafluoroethane (i.e., $CF_3CHClF$ or HCFC-124) to a mixture comprising 2,2-dichloro-1,1,1-trifluoroethane (i.e., $CHCl_2CF_3$ or HCFC-123) and 1,1,1,2,2-pentafluoroethane (i.e., $CF_3CHF_2$ or HFC-125) in addition to unconverted starting materials. The mixture comprising HFC-125 and HCFC-123 may be obtained in the vapor phase by contacting a mixture of HCFC-124a and -124 over the catalysts of this invention optionally in the presence of a diluent selected from the group consisting of HF, HCl, nitrogen, helium, argon, and carbon dioxide. The disproportionation is preferably conducted at about 150° C. to about 400° C., more preferably about 250° C. to about 350° C. If used, the diluent gas, may be present in a molar ratio of diluent to haloethane of from about 1:1 to about 5:1. Preferred contact times are from about 10 seconds to about 60 seconds.

Dehydrofluorination

Included in this invention is a process for decreasing the fluorine content of a halogenated hydrocarbon compound by dehydrofluorinating said halogenated hydrocarbon compound in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent.

Halogenated hydrocarbon compounds suitable as starting materials for the dehydrofluorination process of this invention are typically saturated. Saturated halogenated hydrocarbon compounds suitable for the dehydrofluorination process of this invention include those of the general formula $C_nH_aF_d$, wherein n is an integer from 2 to 6, a is an integer from 1 to 12, d is an integer from 1 to 13, and the sum of a and d is equal to 2n+2. The fluorine content of saturated compounds of the formula $C_nH_aF_d$ may be decreased in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent. This decrease in fluorine content is typically associated with removal of hydrogen fluoride (HF) from the molecule and is referred to herein as dehydrofluorination.

The dehydrofluorination reactions are typically conducted at temperatures of from about 200° C. to about 500° C., preferably from about 300° C. to about 450° C. The contact time in the reactor is typically from about 1 to about 360 seconds and preferably from about 5 to about 120 seconds. Carrying out the dehydrofluorination reactions in the presence of an inert gas such as helium, argon, or nitrogen promotes the dissociation of the fluorinated hydrocarbon compound, but this practice can also lead to difficulties in separation and is not preferred.

The product of dehydrofluorination reaction consists of HF and the unsaturated fluorinated hydrocarbon compound resulting from loss of HF from the starting material. Specific examples of vapor phase dehydrofluorination reactions which may be carried out using the catalysts of this invention include the conversion of $CH_3CHF_2$ to $CH_2\!\!=\!\!CHF$, the conversion of $CH_3CF_3$ to $CH_2\!\!=\!\!CF_2$, the conversion of $CF_3CH_2F$ to $CF_2\!\!=\!\!CHF$, the conversion of $CHF_2CH_2CF_3$ to $CHF\!\!=\!\!CHCF_3$, and the conversion of $CF_3CH_2CF_3$ to $CF_3CH\!\!=\!\!CF_2$.

Of note is a catalytic process for producing fluoroethene (i.e., $CH_2\!\!=\!\!CHF$ or vinyl fluoride) by the dehydrofluorination of a 1,1-difluoroethane (i.e., $CHF_2CH_3$ or HFC-152a). A mixture comprising vinyl fluoride and unconverted HFC-152a may be obtained in the vapor phase by contacting HFC-152a over the catalysts of this invention optionally in the presence of a diluent selected from the group consisting of HF, nitrogen, helium, argon, and carbon dioxide. The dehydrofluorination is preferably conducted at about 150° C. to about 400° C., more preferably about 250° C. to about 350° C. If used, the diluent gas, may be present in a molar ratio of diluent to haloethane of from about 1:1 to about 5:1. Preferred contact times are from about 10 seconds to about 60 seconds.

Chlorodefluorination

Included in this invention is a process for decreasing the fluorine content of a halogenated hydrocarbon compound by reacting said halogenated hydrocarbon compound with hydrogen chloride (HCl) in the vapor phase in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent.

Halogenated hydrocarbon compounds suitable as starting materials for the chlorodefluorination process of this invention may be saturated or unsaturated. Saturated halogenated hydrocarbon compounds suitable for the chlorodefluorination processes of this invention include those of the general formula $C_nH_aCl_cF_d$, wherein n is an integer from 1 to 6, a is an integer from 0 to to 12, c is an integer from 0 to 13, and d is an integer from 1 to 13, and the sum of a, c, and d is equal to 2n+2. Unsaturated halogenated hydrocarbon compounds suitable for the chlorodefluorination process of this invention include those of the general formula $C_pH_eCl_gF_h$, wherein p is an integer from 2 to 6, e is an integer from 0 to 10, g is an integer from 0 to 12, h is an integer from 1 to 11, and the sum of e, g, and h is equal to 2p. The fluorine content of saturated compounds of the formula $C_nH_aCl_cF_d$ and unsaturated compounds of the formula $C_pH_eCl_gF_h$ may be decreased by reacting said compounds in the vapor phase in the presence of a catalyst composition comprising at least one chromium-containing component selected from the group consisting of the crystalline nickel-substituted alpha-chromium oxide described above, the mixed nickel- and cobalt-substituted alpha-chromium oxide described above, and said substituted alpha-chromium oxide which has been treated with a fluorinating agent. Such a process is referred to herein as a vapor phase chlorodefluorination reaction. Chlorodefluorination is disclosed in U.S. Pat. No. 5,345,017 and U.S. Pat. No. 5,763,698 and the teachings of these two patents are hereby incorporated herein by reference.

The chlorodefluorination reactions are typically conducted at temperatures of from about 250° C. to 450° C., preferably from about 300° C. to about 400° C. The contact time in the reactor is typically from about 1 to about 120 seconds and preferably from about 5 to about 60 seconds. The reactions are most conveniently carried out at atmospheric or superatmospheric pressure.

Chlorodefluorinations involving saturated halogenated hydrocarbons are of particular note. The molar ratio of HCl to the saturated halogenated hydrocarbon compound is typically from about 1:1 to about 100:1, preferably from about 3:1 to about 50:1, and most preferably from about 4:1 to about 30:1. In general, with a given catalyst composition, the higher the temperature, the longer the contact time, and the greater the molar ratio of HCl to saturated halogenated hydrocarbon compound, the greater is the conversion to compounds having lower fluorine content. The above variables can be balanced, one against the other, so that the formation of chlorine-substituted products is maximized.

The product of chlorodefluorination reactions typically comprise unreacted HCl, HF, unconverted starting material, and saturated halogenated hydrocarbon compounds having a lower fluorine content than the starting material by virtue of the substitution of one or more fluorine substituents for chlorine. Specific examples of vapor phase chlorodefluorination reactions which may be carried out using the catalysts of this invention include the conversion of $CHF_3$ to a mixture of $CHCl_3$, $CHCl_2F$, and $CHClF_2$, the conversion of $CClF_2CClF_2$ to a mixture of $CCl_3CCl_3$, $CCl_3CCl_2F$, $CCl_3CClF_2$, $CCl_2FCCl_2F$, $CClF_2CCl_2F$, and $CCl_3CF_3$, the conversion of $CF_3CClF_2$ to a mixture of $CCl_3CCl_3$, $CCl_3CCl_2F$, $CCl_3CClF_2$, $CCl_2FCCl_2F$, $CClF_2CCl_2F$, $CCl_3CF_3$, $CClF_2CClF_2$, and $CF_3CCl_2F$, the conversion of $CF_3CCl_2CF_3$ to a mixture of $CF_3CCl_2CClF_2$, $CF_3CCl_2CCl_2F$, $CF_3CCl_2CCl_3$, and $CClF_2CCl_2CCl_3$, and the conversion of $CF_3CH_2CF_3$ to a mixture of $CCl_2\!=\!CHCF_3$ and $CCl_2\!=\!CClCF_3$.

Of note is a catalytic process for producing a mixture containing 1,1-dichloro-3,3,3-trifluoro-1-propene (i.e., $CCl_2\!=\!CHCF_3$ or HCFC-1223za) and 1,1,2-trichloro-3,3,3-trifluoro-1-propene (i.e., $CCl_2\!=\!CClCF_3$ or CFC-1213xa) by the chlorodefluorination of 1,1,1,3,3,3-hexafluoropropane (i.e., $CF_3CH_2CF_3$ or HFC-236fa) by reaction of HFC-236fa with HCl in the vapor phase in the presence of the catalysts of this invention. The reaction is preferably conducted from about 275° C. to about 450° C., more preferably about 300° C. to about 400° C. with a molar ratio of HCl to HFC-236fa of preferably from about 3:1 to about 20:1. Preferred contacts times are from about 1 second to about 40 seconds. Oxygen in the form of air or co-fed with an inert diluent such as nitrogen, helium, or argon may be added along with the reactants or as a separate catalyst treatment, if desired.

The reaction products obtained by the processes of this invention can be separated by conventional techniques, such as with combinations including, but not limited to, scrubbing, decantation, or distillation. Some of the products of the various embodiments of this invention may form one or more azeotropes with each other or with HF.

The processes of this invention can be carried out readily using well known chemical engineering practices.

Utility

Several of the reaction products obtained through use of the catalysts disclosed herein will have desired properties for direct commercial use. For example, $CH_2F_2$ (HFC-32), $CHF_2CF_3$ (HFC-125), $CHF_2CF_3$ (HFC-125), $CH_2FCHF_2$ (HFC-134), $CF_3CH_2CF_3$ (HFC-236fa), and $CF_3CH_2CHF_2$ (HFC-245fa) find application as refrigerants, $CH_2FCF_3$ (HFC-134a) and $CF_3CHFCF_3$ (HFC-227ea) find application as propellants, $CH_2FCHF_2$ (HFC-134) and $CF_3CH_2CHF_2$ (HFC-245fa) find application as blowing agents, and $CHF_2CF_3$ (HFC-125), $CF_3CH_2CF_3$ (HFC-236fa), and $CF_3CHFCF_3$ (HFC-227ea) find application as fire extinguishants.

Other reaction products obtained through the use of this invention are used as chemical intermediates to make useful products. For example, $CCl_3CF_3$ (CFC-113a) can be used to prepare CFC-114a which can then be converted to $CH_2FCF_3$ (HFC-134a) by hydrodechlorination. Similarly, $CF_3CCl_2CF_3$ (CFC-216aa) can be used to prepare $CF_3CH_2CF_3$ (HFC-236fa) by hydrodechlorination and $CF_3CCl\!=\!CF_2$ (CFC-1215zc) can be used to prepare $CF_3CH_2CHF_2$ (HFC-245fa) by hydrogenation.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Catalyst Characterization

Energy Dispersive Spectroscopy (EDS) and Transmission Electron Microscopy (TEM)

In these studies, the crystallites were analyzed using a Philips CM-20 high-resolution transmission electron microscope operated at an accelerating voltage of 200 kV and configured with an Oxford windowless EDS system with a Si(Li) elemental detector. In the EDS analyses, electron-transparent thin sections of samples were used to minimize sample thickness effects such as fluorescence. Also, due to the similarity of their atomic masses, the X-ray absorption cross-sections for Cr. Co, and Ni were assumed to be the same (see the discussion by Zaluzec on pages 121 to 167 in *Introduction to Analytical Electron Microscopy* edited by J. J. Hren, J. I. Goldstein, and D. C. Joy (Plenum Press, New York, 1979). The presence of copper in the EDS of FIGS. 1, 2, 3, 4, and 5 is due to the TEM grid and background in the microscope.

X-Ray Absorption Spectroscopy (XAS) and X-Ray Powder Diffraction (XRD)

XRD data were obtained and analyzed according to methods described by Warren in *X-Ray Diffraction* (Addison-Wesley, Reading, Mass., 1969). XAS data were obtained at beamline 5BMD, DND-CAT, of the Advanced Photon Source, Argonne National Laboratory. XAS data were obtained and analyzed using the methods described in Koningsberger and Prins in *X-ray Absorption: Principles, Applications, Techniques of EXAFS, SEXAFS and XANES* (John Wiley & Sons, New York, 1988). Spectra were obtained for the K edges of Cr, Co, and Ni. Cr edges were obtained in transmission geometry, while Co and Ni edges were obtained in fluorescence mode, due to their low concentrations.

Use of the Advanced Photon Source was supported by the U.S. Department of Energy, Office of Basic Energy Sciences, under Contract No. W-31-109-Eng-38.

Catalyst Preparation

Preparation Example 1

Preparation of 95% Chromium/3% Cobalt/2% Nickel Catalyst (6.2 eq. of excess $NH_4NO_3$; 400° C.)

A solution of 380.14 g $Cr(NO_3)_3[9(H_2O)]$ (0.95 mole), 8.73 g $Co(NO_3)_2[6(H_2O)]$ (0.030 mole), and 5.82 g $Ni(NO_3)_2[6(H_2O)]$ (0.020 mole) was prepared in 1000 mL of deionized water. The solution was increased from pH 3.1 to pH 8.5 by treatment with 7.4M aqueous ammonium hydroxide. The slurry was stirred at room temperature for 21 hours at pH 8.5. The mixture was then treated with a solution of 472.24 g of $NH_4(NO_3)$ (5.90 moles) dissolved in 500 mL of water. The slurry was stirred for one hour at room temperature and then dried at 110-120° C. in air for about 96 hours. The dried solids was crushed to a powder and then placed in a covered crucible and calcined at 400° C. for 24 hours in air.

Analysis by TEM and EDS indicated the majority of the crystals were <50 nm in size with uniform incorporation of both cobalt and nickel into the $\alpha$-$Cr_2O_3$ lattice. No spinel-like phases were detected. Analysis of the sample by XRD and XAS confirmed that the crystallites had an $\alpha$-$Cr_2O_3$ structure and that the average oxidation state of cobalt was 2.89. The amount of cobalt incorporation in the $\alpha$-$Cr_2O_3$ lattice was about 2.5-2.7 atom %. XRD confirmed that nickel appeared to be fully incorporated into the $\alpha$-$Cr_2O_3$ lattice as well.

Preparation Example 2

Preparation of 98% Chromium/1% Cobalt 1% Nickel Catalyst (550° C.)

$[Cr(NH_3)_6]Cl_3$ (16.7755 g, 64.6 mmoles), and $[Co(NH_3)_6]Cl_3$ (0.1757 g, 0.657 mmole), and $Ni(NO_3)_2[6H_2O]$ (0.1891 g, 0.650 mmole) were dissolved in deionized water. Aqueous ammonium hydroxide was then added to the solution until precipitation was complete. The resulting precipitate was filtered and dried in air at 110° C. for 12 hours. The resulting product was ground thoroughly in an agate mortar and then heated at 550° C. in air for 12 hours.

Analysis of the sample by TEM and EDS indicated a small amount of a spinel phase containing cobalt, nickel, and chromium; this phase was richer in cobalt than nickel. The $\alpha$-$Cr_2O_3$ phase was present in the form of 100-400 nm crystals; this phase contained both nickel and cobalt with a slight excess of nickel. XAS indicated that cobalt was completely incorporated into the $\alpha$-$Cr_2O_3$ lattice. The Ni near edge structure was similar to the composition of PREPARATION EXAMPLE 1 was consistent with some incorporation of nickel into the $\alpha$-$Cr_2O_3$ lattice.

Preparation Example 3

Preparation of 98% Chromium/2% Nickel Catalyst (550° C.)

$[Cr(NH_3)_6]Cl_3$ (16.7727 g, 64.38 mmoles) and $Ni(NO_3)_2[6H_2O]$ (0.3783 g, 1.30 mmoles) were dissolved in deionized water. Aqueous ammonium hydroxide was then added to the solution until precipitation was complete. The resulting precipitate was filtered and dried in air at 110° C. for 12 hours. The dried product was then ground thoroughly in an agate mortar and then heated at 550° C. in air for 12 hours.

Analysis of the sample by TEM and EDS indicated the presence of a nickel-substituted $\alpha$-$Cr_2O_3$ phase mostly in the form of 200 nm crystals; some of the crystals were in the 300-400 nm size range. There was no evidence for a nickel/chromium spinel phase. Some nickel was incorporated into the $\alpha$-$Cr_2O_3$ lattice because the Ni near edge structure was similar to the catalyst of PREPARATION EXAMPLE 1.

Preparation Example 4

Preparation of 98% Chromium/2% Nickel Catalyst (550° C.)

$Cr(NO_3)_3[9(H_2O)]$,(50.5 g, 0.126 mole) and $Ni(NO_3)_2[6(H_2O)]$ (0.816 g, 0.00280 mole) were weighed into a porcelain crucible and melted together with stirring in the open air. The mixture was heated to decomposition. A portion of the resulting solid was then calcined in a furnace at 550° C. for 12 hours.

In a manner similar to that above, nickel/chromium oxide compositions having the bulk composition 0.5 atom % nickel/99.5 atom % chromium and 1 atom % nickel/99 atom % chromium were prepared and calcined at 550° C.

TEM and EDS analyses of the 98/2 Cr/Ni and the 99.5/0.5 Cr/Ni compositions indicated that these samples contained nickel-substituted crystals of $\alpha$-$Cr_2O_3$ ranging in size from 200 to 400 nm. A spinel phase with a Ni/Cr ratio of about 3/1 having crystallite sizes ranging from about 10 to 30 nm was also present especially in the 98/2 Cr/Ni sample.

XAS analysis of these three samples was consistent with nickel incorporation into the $\alpha$-$Cr_2O_3$ lattice. The average oxidation state of chromium was about +3.20 with a phase containing a small amount of $Cr^{+6}$ also present.

Preparation Example 5

Preparation of 98% Chromium/2% Nickel Catalyst (900° C.)

A solution of 392.15 g $Cr(NO_3)_3[9(H_2O)]$ (0.98 mole) dissolved in 1 L of deionized water was treated with 20 mL of a 1 molar solution of aqueous $Ni(NO_3)_2[6(H_2O)]$ (0.020 mole). The resulting solution was treated dropwise with 225 mL of 7.4M aqueous; the pH increased from 1.96 to 8.53 during the addition. The slurry was stirred at room temperature for 24 hours and then evaporated to dryness in air at 110° C. and held at that temperature overnight. The dried catalyst was ground to a powder and then calcined in air at 900° C. for 20 hours.

TEM and EDS analyses indicated that this composition consisted of crystals of α-Cr$_2$O$_3$ ranging from about 300 to 400 nm in size with approximately uniform incorporation of nickel.

Preparation Example 6

Preparation of 95% Chromium/5% Nickel Catalyst (900° C.)

A solution of 380.14 g Cr(NO$_3$)$_3$[9(H$_2$O)] (0.95 mole) dissolved in 1 L of deionized water was treated with 50 mL of a 1 molar solution of aqueous Ni(NO$_3$)$_2$[6(H$_2$O)] (0.050 mole). The catalyst was treated with aqueous ammonium hydroxide, dried, and calcined as in PREPARATION EXAMPLE 5.

Preparation Example 7

Preparation of 98% Chromium/2% Nickel Catalyst (400° C.)

A solution of 588.3 g Cr(NO$_3$)$_3$[9(H$_2$O)] (1.47 moles) and 8.72 g (0.030 mole) Ni(NO$_3$)$_2$[6(H$_2$O)] dissolved in 1.5 L of deionized water was treated with 7.4M aqueous ammonium hydroxide until the pH reached 8.5. The addition of ammonium hydroxide took 1.5 hours. The slurry was stirred at room temperature for 24 hours; ammonium hydroxide was added occasionally to keep the pH at about 8.5. The mixture was then evaporated to dryness in air at 110° C. over the course of 40 hours. The dried catalyst was ground to a powder and then calcined in air at 400° C. for 24 hours.

TEM and EDS analyses indicated that this sample consisted of crystals of α-Cr$_2$O$_3$ ranging in size from 20 to 100 nm with approximately uniform incorporation of nickel. There is no evidence for the formation of a second spinel phase in this sample.

Analysis of the sample by XRD and XAS confirmed that the crystallites had an α-Cr$_2$O$_3$ structure. The environment around the Ni atom was very similar to that of the environment around the chromium atoms. The amount of nickel incorporation in the α-Cr$_2$O$_3$ lattice was about 1.6 atom %. No spinel phase was observed.

Preparation Example 8

Preparation of 95% Chromium/5% Nickel Catalyst (400° C.)

The procedure of PREPARATION EXAMPLE 7 was repeated using a solution of 760.3 g Cr(NO$_3$)$_3$[9(H$_2$O)] (1.90 moles) and 29.08 g (0.10 mole) Ni(NO$_3$)$_2$[6(H$_2$O)] dissolved in 2 L of deionized water. After the addition of ammonium hydroxide and evaporation at 110° C., the solid was calcined in air at 400° C. for 24 hours.

TEM and EDS analyses indicated that this sample consisted of crystals of α-Cr$_2$O$_3$ with a much wider particle size range (from 10 to 200 nm) than the composition of PREPARATION EXAMPLE 7 with approximately uniform incorporation of nickel into the alpha-chromium oxide lattice. There was no evidence for the formation of a second spinel phase.

Analysis of the sample by XRD and XAS confirmed that the crystallites had an α-Cr$_2$O$_3$ structure. The environment around the Ni atom was very similar to that of the environment around the chromium atoms. The amount of nickel incorporation in the α-Cr$_2$O$_3$ lattice was about 2.0 atom %. A small amount of a second nickel-containing phase was observed.

General Procedure for Product Analysis

The following general procedure is illustrative of the method used. Part of the total reactor effluent was sampled on-line for organic product analysis using a gas chromatograph equipped a mass selective detector (GC-MS). The gas chromatography was accomplished with a 20 ft. (6.1 m) long×⅛ in. (0.32 cm) diameter tubing containing Krytox® perfluorinated polyether on an inert carbon support. The helium flow was 30 mL/min (5.0×10$^{-7}$ m$^3$/s). Gas chromatographic conditions were 60° C. for an initial hold period of three minutes followed by temperature programming to 200° C. at a rate of 6° C./minute.

The bulk of the reactor effluent containing organic products and also inorganic acids such as HCl and HF was treated with aqueous caustic prior to disposal.

All vapor reactions were conducted at a nominal pressure of one atmosphere.

| Legend | |
|---|---|
| 112 is CCl$_2$FCCl$_2$F | 113 is CCl$_2$FCClF$_2$ |
| 113a is CCl$_3$CF$_3$ | 114 is CClF$_2$CClF$_2$ |
| 114a is CF$_3$CCl$_2$F | 115 is CF$_3$CClF$_2$ |
| 214ab is CF$_3$CCl$_2$CCl$_2$F | 215aa is CF$_3$CCl$_2$CClF$_2$ |
| 215bb is CCl$_2$FCClFCF$_3$ | 216aa is CF$_3$CCl$_2$CF$_3$ |
| 216ba is CClF$_2$CClFCF$_3$ | 216ca is CClF$_2$CF$_2$CClF$_2$ |
| 216cb is CCl$_2$FCF$_2$CF$_3$ | 217ba is CF$_3$CClFCF$_3$ |
| 217ca is CClF$_2$CF$_2$CF$_3$ | 218 is C$_3$F$_8$ |
| 226da is CF$_3$CHClCF$_3$ | 236fa is CF$_3$CH$_2$CF$_3$ |
| 1213xa is CF$_3$CCl=CCl$_2$ | 1214 is C$_3$Cl$_2$F$_4$ |
| 1215 is C$_3$ClF$_5$ | 13 is CClF$_3$ |
| PCE is CCl$_2$=CCl$_2$ | |

Example 9

Nickel-substituted chromium oxide (Cr/Ni 98/2 calcined at 400° C., 29.6 g, 20 mL, −12 to +20 mesh, (1.68 to 0.84 mm)), prepared as described in PREPARATION EXAMPLE 7, was placed in a ⅝" (1.58 cm) diameter Inconel™ nickel alloy reactor tube heated in a fluidized sand bath. The catalyst was heated from 88° C. to 175° C. in a flow of nitrogen (50 cc/min, 8.3×10$^{-7}$ m$^3$/s) over the course of about 40 minutes. HF and N$_2$ were then co-fed to the reactor at flow rates of 50 cc/min (8.3×10$^{-7}$ m$^3$/s) each. After 1.8 hours, the nitrogen flow was decreased to 20 cc/min (3.3'10$^{-7}$ m$^3$/s) and the HF flow increased to 80 cc/min (1.3×10$^{-6}$ m$^3$/s). The reactor temperature was gradually increased to 247° C. over a 1.6 hour period and then purged with nitrogen (20 cc/min, 3.3×10$^{-7}$ m$^3$/s) overnight. The HF treatment was resumed with a flow rate of 80 cc/min (1.3×10$^{-6}$ m$^3$/s and a nitrogen co-fed at 20 cc/min (3.3×10$^{-7}$ m$^3$/s). These gas flows were maintained for 1.8 hours as the temperature was increased from 249° C. to 402° C. The reactor temperature was held at 402° C. for 0.5 hour. The nitrogen flow was then shut off and fluorination of CFC-1213xa was begun at 300° C. with a 20:1 molar ratio of HF to CFC-1213xa at a contact time of 15 seconds. Under these conditions, the reactor effluent was 94.4 GC area % HCFC-226da and 4.1% CFC-216aa at 100% conversion of the CFC-1213xa. Chlorine was then co-fed to the reactor; the molar ratio of HF:CFC-1213xa:Cl2 was 20:1:4. The composition of the reactor effluent at 350° C. is given below.

| Component | GC Area % |
| --- | --- |
| HCFC-226da | 0.7 |
| CFC-216ba | 15.3 |
| CFC-216aa | 55.6 |
| CFC-217ba | 15.8 |
| CFC-217ca | 0.9 |
| CFC-215aa | 11.1 |
| CFC-215bb | 0.09 |
| Other | 0.6 |

Other products included PCE, CFC-114, CFC-115, FC-218, CFC-1215.

Example 10

Nickel-substituted chromium oxide (Cr/Ni 95/5 calcined at 400° C., 29.2 g, 20 mL, −12 to +20 mesh, (1.68 to 0.84 mm)), prepared as described in PREPARATION EXAMPLE 8, was placed in a ⅝" (1.58 cm) diameter Inconel™ nickel alloy reactor tube heated in a fluidized sand bath. The catalyst was heated from 68° C. to 176° C. in a flow of nitrogen (50 cc/min, $8.3 \times 10^{-7}$ m$^3$/s) over the course of about 1 hour. HF and N$_2$ were then co-fed to the reactor at flow rates of 50 cc/min ($8.3 \times 10^{-7}$ m$^3$/s) each. After 1.3 hours, the nitrogen flow was decreased to 20 cc/min ($3.3 \times 10^{-7}$ m$^3$/s) and the HF flow increased to 80 cc/min ($1.3 \times 10^{-6}$ m$^3$/s). The reactor temperature was gradually increased from 176° C. to 402° C. over a 3.3 hour period and then held at 400° C. for 0.5 hour. The HF flow was then shut off and the reactor purged with nitrogen while it was allowed to cool to 300° C. Fluorination of CFC-1213xa was begun at 300° C. with a 20:1 molar ratio of HF to CFC-1213xa at a contact time of 15 seconds. Under these conditions, the reactor effluent was 93.4 GC area % HCFC-226da and 4.9% CFC-216aa at 100% conversion of the CFC-1213xa. Chlorine was then co-fed to the reactor; the molar ratio of HF:CFC-1213x a:Cl2 was 20:1:4 (15 second contact time). The composition of the reactor effluent at 350° C. is given below.

| Component | GC Area % |
| --- | --- |
| HCFC-226da | 1.3 |
| CFC-216ba | 25.2 |
| CFC-216aa | 30.1 |
| CFC-217ba | 18.1 |
| CFC-217ca | 1.0 |
| CFC-215aa | 22.9 |
| CFC-215bb | 0.2 |
| Other | 1.2 |

Other products included CFC-13, CFC-114, CFC-114a, CFC-115, CFC-1215, CFC-216cb, CFC-214ab, PCE.

Example 11

Nickel-substituted chromium oxide (Cr/Ni 98/2 calcined at 900° C., 40.27 g, 25 mL, −12 to +20 mesh, (1.68 to 0.84 mm)), prepared as described in PREPARATION EXAMPLE 5, was placed in a ⅝" (1.58 cm) diameter Inconel™ nickel alloy reactor tube heated in a fluidized sand bath. The catalyst was heated from 57° C. to 175° C. in a flow of nitrogen (50 cc/min, $8.3 \times 10^{-7}$ m$^3$/s) over the course of about one hour. HF and N$_2$ were then co-fed to the reactor at flow rates of 50 cc/min ($8.3 \times 10^{-7}$ m$^3$/s) each. After 11 minutes, the nitrogen flow was decreased to 20 cc/min ($3.3 \times 10^{-7}$ m$^3$/s) and the HF flow increased to 80 cc/min ($1.3 \times 10^{-6}$ m$^3$/s). The reactor temperature was gradually increased to 400° C. during a 2.7 hour period and maintained at 400° C. for an additional hour. At the end of this period, the HF flow was stopped and the reactor cooled to 280° C. and purged with under nitrogen overnight. Chlorofluorination of CFC-1213xa was begun at 280° C. with HF, CFC-1213xa, and chlorine in molar ratios of 20:1:4 at a contact time of 30 seconds. The composition of the reactor effluent at 340° C. is given below.

| Component | GC Area % |
| --- | --- |
| HCFC-226da | 0.8 |
| CFC-216ba | 26.2 |
| CFC-216aa | 25.5 |
| CFC-216ca | 1.1 |
| CFC-217ba | 8.3 |
| CFC-215aa | 35.3 |
| CFC-215bb | 1.9 |
| Other | 0.9 |

Other products included CFC-1215, CFC-217ca

Example 12

Nickel-substituted chromium oxide (Cr/Ni 95/5 calcined at 900° C., 40.27 g, 25 mL, −12 to +20 mesh, (1.68 to 0.84 mm)), prepared as described in PREPARATION EXAMPLE 6, was placed in a ⅝" (1.58 cm) diameter Inconel™ nickel alloy reactor tube heated in a fluidized sand bath. The catalyst was heated at 100° C. in a flow of nitrogen (50 cc/min, ($8.3 \times 10^{-7}$ m$^3$/s) for 40 minutes. HF and N$_2$ were then co-fed to the reactor at flow rates of 50 cc/min ($8.3 \times 10^{-7}$ m$^3$/s) each. After 30 minutes, the nitrogen flow was decreased to 20 cc/min ($3.3 \times 10^{-7}$ m$^3$/s) and the HF flow increased to 80 cc/min ($1.3 \times 10^{-6}$ m$^3$/s). The reactor temperature was then gradually increased to 401° C. during a 5 hour period. At the end of this period, the HF flow was stopped and the reactor cooled to 280° C. and purged with under nitrogen overnight. Chlorofluorination of CFC-1213xa was begun at 280° C. with HF, CFC-1213xa, and chlorine co-fed to the reactor in molar ratios of 20:1:4 at a contact time of 30 seconds. The composition of the reactor effluent at 340° C. is given below.

| Component | GC Area % |
| --- | --- |
| HCFC-226da | 1.1 |
| CFC-216ba | 23.7 |
| CFC-216aa | 19.2 |
| CFC-216ca | 1.2 |
| CFC-217ba | 11.9 |
| CFC-215aa | 29.9 |
| CFC-215bb | 12.0 |
| Other | 0.3 |

Other products included CFC-1215, CFC-1214.

Example 13

A mixed nickel- and cobalt-substituted chromium oxide (Cr/Co/Ni 95/3/2, 26.37 g, 19 mL, −12 to +20 mesh, (1.68 to 0.84 mm)), prepared as described in PREPARATION EXAMPLE 1, was placed in a ⅝" (1.58 cm) diameter Inconel™ nickel alloy reactor tube heated in a fluidized sand bath. The catalyst was heated from 81° C. to 175° C. in a flow of nitrogen (50 cc/min, $8.3 \times 10^{-7}$ m$^3$/s) over the course of about one hour. HF and N$_2$ were then co-fed to the reactor at flow rates of 50 cc/min ($8.3 \times 10^{-7}$ m$^3$/s) each. After 0.3 hour, the nitrogen flow was decreased to 20 cc/min ($3.3\times10^{-7}$ m$^3$/s) and the HF flow increased to 80 cc/min ($1.3\times10^{-6}$ m$^3$/s). The reactor temperature was gradually increased to 400° C. during a 3.6 hour period. The HF flow was then stopped and the reactor cooled to 298° C. under 20 sccm ($3.3\times10^{-7}$ m$^3$/s) nitrogen flow. Chlorofluorination of CFC-1213xa began at 300° C. with HF, CFC-1213xa, and chlorine were co-fed to the reactor in molar ratio of 20:1:4, respectively, at a contact time of 15 seconds. The GC-MS analyses of the reactor effluent at 320° C. (molar feed ratio of 20:1:4) and 375° C. (molar feed ratio of 30:1:2) is given below.

|  | GC Area % | |
| --- | --- | --- |
| Component | 320° C. | 375° C. |
| HCFC-226da | 1.4 | 1.0 |
| CFC-216ba | 21.2 | 16.3 |
| CFC-216aa | 22.0 | 40.8 |
| CFC-217ba | 16.6 | 34.0 |
| CFC-215aa | 35.9 | 5.0 |
| CFC-217ca | 0.7 | 1.9 |
| CFC-216cb | 1.0 | — |
| Other | 1.2 | |

Other products included CFC-1215, CFC-114, CFC-114a, HCFC-225da, CFC-113.

What is claimed is:

1. A crystalline alpha-chromium oxide where from about 0.05 atom % to about 2 atom % of the chromium atoms in the alpha-chromium oxide lattice are substituted by nickel atoms, and optionally, additional chromium atoms in the alpha-chromium oxide lattice are substituted by trivalent cobalt atoms, provided that the total amount of the nickel atoms and the trivalent cobalt atoms in the alpha-chromium oxide lattice is no more than 6 atom %.

2. A chromium-containing catalyst composition comprising as a chromium-containing component the crystalline substituted alpha-chromium oxide of claim 1.

3. A chromium-containing catalyst composition comprising a chromium-containing component prepared by treating the crystalline substituted alpha-chromium oxide of claim 1 with a fluorinating agent.

4. A process for changing the fluorine distribution in a hydrocarbon or a halogenated hydrocarbon in the presence of a catalyst, characterized by:

using as the catalyst a composition comprising at least one chromium-containing component selected from the group consisting of the crystalline substituted alpha-chromium oxide of claim 1 and a crystalline substituted alpha-chromium oxide of claim 1 which has been treated with a fluorinating agent.

5. The process of claim 4 wherein the fluorine content of a halogenated hydrocarbon compound or an unsaturated hydrocarbon compound is increased by reacting said compound with hydrogen fluoride in the vapor phase in the presence of said catalyst composition.

6. The process of claim 4 wherein the fluorine content of a halogenated hydrocarbon compound or a hydrocarbon compound is increased by reacting said compound with HF and Cl$_2$ in the vapor phase in the presence of said catalyst composition.

7. The process of claim 4 wherein the fluorine distribution in a halogenated hydrocarbon compound is changed by isomerizing said halogenated hydrocarbon compound in the presence of said catalyst composition.

8. The process of claim 4 wherein the fluorine distribution in a halogenated hydrocarbon compound is changed by disproportionating said halogenated hydrocarbon compound in the vapor phase in the presence of said catalyst composition.

9. The process of claim 4 wherein the fluorine content of a halogenated hydrocarbon compound is decreased by dehydrofluorinating said halogenated hydrocarbon compound in the presence of said catalyst composition.

10. The process of claim 4 wherein the fluorine content of a halogenated hydrocarbon compound is decreased by reacting said halogenated hydrocarbon compound with hydrogen chloride in the vapor phase in the presence of said catalyst composition.

11. A method for preparing a composition comprising the crystalline substituted alpha-chromium oxide of claim 1, comprising:

(a) co-precipitating a solid by adding ammonium hydroxide to an aqueous solution of a soluble divalent nickel salt, a soluble trivalent chromium salt, and optionally, a soluble divalent or trivalent cobalt salt, that contains at least three moles of nitrate per mole of chromium in the solution, has a nickel concentration of from about 0.05 mole % to about 2 mole % of the total of nickel, chromium, and cobalt (if present) in the solution, and has a combined concentration of nickel and cobalt (if present) of no more than 6 mole % of the total of nickel, chromium, and cobalt (if present) in the solution; and after at least three moles of ammonium per mole of chromium has been added to the solution;

(b) collecting co-precipitated solid formed in (a);

(c) drying the collected solid; and (d) calcining the dried solid.

12. The method of claim 11 wherein the soluble nickel salt is a nitrate or a hydrated nitrate.

13. The method of claim 12 wherein the soluble chromium salt is a nitrate or a hydrated nitrate.

14. The method of claim 13 wherein more than three moles of ammonium nitrate per mole of chromium is present in the aqueous solution.

* * * * *